United States Patent
Jiang et al.

(10) Patent No.: US 11,149,271 B2
(45) Date of Patent: Oct. 19, 2021

(54) METHOD AND PHARMACEUTICAL COMPOSITION FOR TREATING CANCER

(71) Applicant: Macau University of Science and Technology, Taipa (MO)

(72) Inventors: Zhi-Hong Jiang, Taipa (MO); Tong-Meng Yan, Taipa (MO); Kai-Yue Cao, Taipa (MO)

(*) Notice: Subject to any disclaimer, the term of this patent is extended or adjusted under 35 U.S.C. 154(b) by 0 days.

(21) Appl. No.: 16/120,606

(22) Filed: Sep. 4, 2018

(65) Prior Publication Data

US 2020/0071695 A1 Mar. 5, 2020

(51) Int. Cl.
*C12N 15/113* (2010.01)
*A61P 35/00* (2006.01)

(52) U.S. Cl.
CPC ............ *C12N 15/113* (2013.01); *A61P 35/00* (2018.01)

(58) Field of Classification Search
CPC .................... C12N 15/113; C12N 2310/14
See application file for complete search history.

(56) References Cited

U.S. PATENT DOCUMENTS

| 2002/0142319 A1* | 10/2002 | Gorlach | ............... | C12Q 1/6895 |
| | | | | 435/6.13 |
| 2009/0239815 A1* | 9/2009 | Litman | .................. | C07H 21/02 |
| | | | | 514/44 R |
| 2013/0137752 A1* | 5/2013 | Brown | .................... | A61P 43/00 |
| | | | | 514/44 A |

OTHER PUBLICATIONS

Hao et al. Physiologia Plantarum 146: 388-403 (Year: 2012).*
Rushi S. Patel et al, 2011, High resolution of micro RNA signatures in human whole saliva.
Rosemary Kanasty et al, 2013, Delivery materials for siRNA therapeutics.
Guilherme Loss-Morais et al, 2013, Description of plant tRNA-derived RNA fragments (tRFs) associated with argonaute and identification of their putative targets.
Cell Research (2015) 25:521-524. doi:10.1038/cr.2015.25; published online Feb. 27, 2015, A novel chemopreventive strategy based on therapeutic microRNAs produced in plants.
Rani Goodarzi, et al., (2015), Endogenous tRNA-Derived Fragments Suppress Breast Cancer Progression via YBX1 Displacement.
Zhen Zhou, et al, 2015, Honeysuckle-encoded atypical microRNA2911 directly targets influenza A viruses.
Veronica Balatti, et al, 2017, Role of the tRNA-Derived Small RNAs in Cancer—New Potential Biomarkers and Target for Therapy.

* cited by examiner

*Primary Examiner* — Brian Whiteman
(74) *Attorney, Agent, or Firm* — Renner, Kenner, Greive, Bobak, Taylor & Weber

(57) ABSTRACT

A method of treating a subject suffering from cancer includes administering an effective amount of a RNA molecule to the subject, wherein the RNA molecule is isolated or derived from a plant of the genus *Taxus*. A method of inhibiting growth or proliferation of cancer cells includes contacting cancer cells with the RNA molecule; and a pharmaceutical composition for treating cancer includes the RNA molecule and a pharmaceutically tolerable excipient. Also a double-stranded RNA molecule and a recombinant vector include the double-stranded RNA molecule.

18 Claims, 14 Drawing Sheets

Specification includes a Sequence Listing.

METHOD AND PHARMACEUTICAL COMPOSITION FOR TREATING CANCER

SEQUENCE LISTING

The Sequence Listing file entitled "sequencelisting" having a size of 43,663 bytes and a creation date of Sep. 4, 2018, that was filed with the patent application is incorporated herein by reference in its entirety

TECHNICAL FIELD

The present invention relates to a method of treating a subject suffering from cancer by administering a nucleic acid to the subject. Said nucleic acid is in particular but not exclusively a RNA molecule. The invention further relates to a pharmaceutical composition comprising a nucleic acid for the treatment and use thereof.

BACKGROUND OF THE INVENTION

Cancer has become the most common disease causing death worldwide. Traditional Chinese medicines (TCMs) have been applied for treating and preventing cancer whereas lots of research efforts have been contributed to investigate the effectiveness of isolated small molecules such as alkaloids, terpenoids, flavonoids or the like in treating cancer. Some alkaloids are found to have effect in inhibiting cancer such as by enhancing the efficacy of an anti-cancer drug. However, most of them are often toxic to human. Also, macromolecules such as DNAs, RNAs, and proteins are generally considered unstable and have poor effect in living human body and therefore have not been widely considered as suitable in said treatment.

Currently, some studies show that non-coding RNAs (ncRNAs) such as microRNAs have diverse regulatory roles through targeting different aspects of RNA transcription or post-transcription process in nearly all eukaryotic organisms. Mlotshwa, S. et al. (*Cell research* 2015, 25 (4), 521-4) suggested that exogenous plant microRNAs in foods could be taken up by the mammalian digestive tract and trafficked via the bloodstream to a variety of tissue cells, where they are capable of regulating the expression of mammalian genes. Goodarzi, H. et al. (*Cell* 2015, 161 (4), 790-802) revealed that endogenous tRNA derived fragments could suppress the stability of multiple oncogenic transcripts in breast cancer cells through binding and antagonizing activities of pathogenesis-related RNA-binding proteins. Nevertheless, there still remains a need to derive effective molecules from various sources such as plants for treatments.

*Taxus chinensis* (Pilger) Rehd. var. *mairei*, a species from the family of Taxaceae, is an ornamental evergreen shrub or tree widely distributed in high elevations of China. As an important medicinal plant, it has been exploited for production of small molecular anti-cancer drugs such as paclitaxel which is also called Taxol. However, patients have been found to develop resistance against commonly used drugs including Taxol and therefore there remains a continuing need for new and improved treatments for patients with cancer and for those having resistance against commonly used drugs and/or associated with different complications.

SUMMARY OF THE INVENTION

In a first aspect, the invention provides a method of treating a subject suffering from cancer, said method comprising the step of administering an effective amount of a RNA molecule said subject. The RNA molecule administered according to the invention is isolated or derived from a plant of the genus *Taxus*.

In an embodiment, the RNA molecule comprises a sequence selected from SEQ ID NO: 1 to SEQ ID NO: 100 or a functional variant or homologue thereof.

Preferably, the RNA molecule of the invention has a sequence length of from about 50 to 200 nucleotides or 10 to 30 base pairs.

In an embodiment, the RNA molecule is a non-coding molecule in particular a transfer RNA molecule.

In an alternative embodiment, the RNA molecule is a double-stranded RNA molecule comprising a sense sequence selected from SEQ ID NO: 1 to SEQ ID NO: 100 or a functional variant or homologue therefore, and a complementary antisense sequence.

In another aspect, the invention provides a method of inhibiting growth or proliferation of cancer cells comprising a step of contacting said cancer cells with an effective amount of a RNA molecule isolated or derived from a plant of the genus *Taxus*.

In an example embodiment, the cancer cells of the present invention are ovarian cancer cells, liver cancer cells, breast cancer cells, colorectal cancer cells, or lung cancer cells.

In a further aspect, the invention pertains to a pharmaceutical composition for treating cancer. The pharmaceutical composition comprises an RNA molecule and a pharmaceutically tolerable excipient, wherein said RNA molecule is isolated or derived from a plant of the genus *Taxus*.

Still further, the invention relates to a double-stranded RNA molecule comprising a sense sequence selected from SEQ ID NO: 1 to SEQ ID NO: 100 or a functional variant or homologue therefore, a complementary antisense sequence, and optionally a 3' overhang.

In another aspect, the invention pertains to a recombinant vector comprising the double-stranded RNA molecule.

The invention provides a novel and effective approach for treating cancers from various origins by administration of a RNA molecule that is isolated or derived from a plant of the genus *Taxus*, or in particular a RNA molecule comprising a sequence selected from SEQ ID NO: 1 to 100. Administration of said RNA molecule is also suitable for inhibiting growth or proliferation of cancer cells. The inventors have found that non-coding RNA molecules isolated from a plant of the genus *Taxus*, particularly transfer RNA molecules, and RNA molecules derived from *Taxus* are particularly useful in treatment of cancer. The RNA molecules with a sequence length of about 10 to 200 nucleotides are highly effective at inhibiting growth and proliferation of cancer cells in vitro and exhibit an antitumor effect in vivo. Said RNA molecules are also effective against Taxol-resistant cell lines. Further, the pharmaceutical composition comprising the RNA molecule that is isolated or derived from a plant of the genus *Taxus* and a pharmaceutically tolerant excipient can act directly on the cancer cells or tumor, and therefore can have a faster-acting therapeutic effect.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 2:
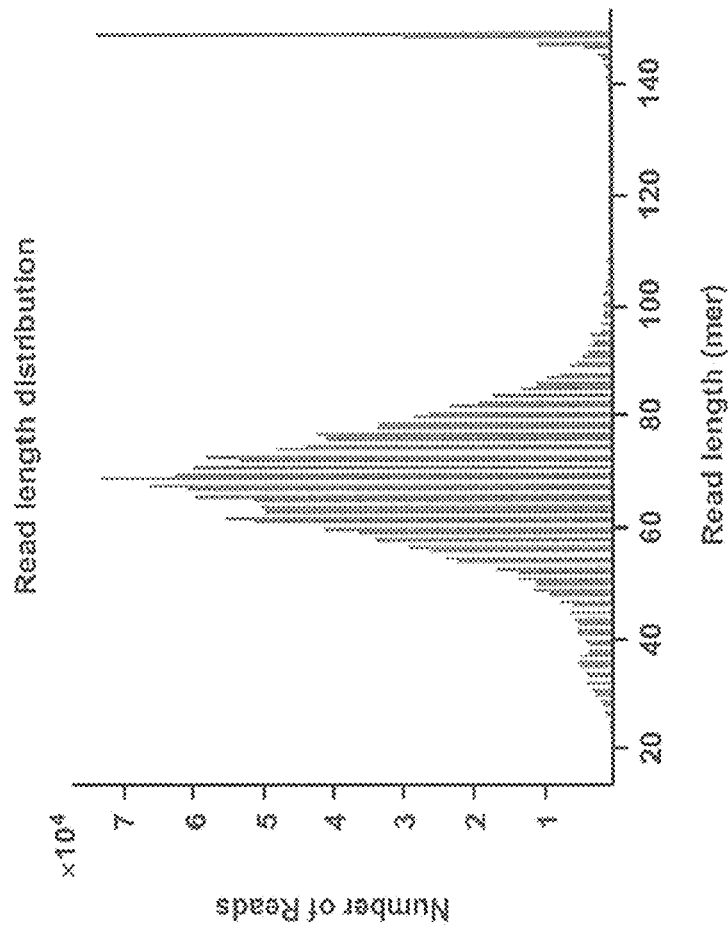
FIG. 2 is a bar chart showing read length distribution of transfer RNAs from *Taxus chinensis* (Pilger) Rehd. var. *mairei* in accordance with an example embodiment.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a method of treating a subject suffering from cancer. The method comprises a step of administering an effective amount of a RNA molecule to said subject. The RNA molecule administered according to the present invention may be naturally present, modified or artificially synthesized according to the sequences disclosed in the present invention, and preferably the RNA molecule is isolated or derived from a plant of the genus *Taxus*. The RNA molecule of the present invention is not provided in the form of boiled extract obtained from the plant such as decoction, as it would be appreciated that RNA molecule is susceptible to spontaneous degradation at elevated temperature, alkaline pH, and the presence of nucleases or divalent metal ions. In an embodiment, the RNA molecule of the present invention is provided together with a gene delivery carrier which will be described in detail later.

The RNA molecule of the present invention has a sequence length of from about 10 to 200 nucleotides which can be regarded as a small RNA molecule. Preferably, the RNA molecule has a sequence length of from about 50 to about 200 nucleotides, from about 60 to about 150 nucleotides, in particular from about 70 to about 100 nucleotides.

The RNA molecule of the present invention comprises a sequence selected from SEQ ID NO: 1 to SEQ ID NO: 100 or a functional variant or homologue thereof. The term "functional variant" of the RNA molecule refers to a molecule substantially similar to said RNA molecule with one or more sequence alterations that do not affect the biological activity or function of the RNA molecule. The alterations in sequence that do not affect the functional properties of the resultant RNA molecules are well known in the art. For example, nucleotide changes which result in alteration of the −5'-terminal and −3'-terminal portions of the molecules would not be expected to alter the activity of the polynucleotides. In an embodiment, the RNA molecule of the present invention comprises at least one modified nucleoside selected from inosine, 1-methyladenosine, 2-methyladenosine, N6-methyladenosine, N6-isopentenyladenosine, 2'-O-methyladenosine, N6-acetyladenosine, 1-methylinosine, pseudouridine, dihydrouridine, or 2-methylthio-N6-methyladenosine.

In particular, the functional variant of the RNA molecule has at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to the non-variant RNA molecule according to the present invention.

The term "homologue" used herein refers to nucleotides having a sequence identity of at least 50%, at least 60%, at least 70%, at least 80%, at least 90% or at least 95% to the RNA molecules according to the present invention. In an embodiment, the homologue of the RNA molecule has at least 90%, 91%, 92%, 93%, 94%, 95%, 96%, 97%, 98%, or 99% overall sequence identity to the RNA molecule.

In an embodiment, the RNA molecule is a non-coding molecule preferably selected from a transfer RNA molecule, a ribosomal RNA molecule, a micro RNA molecule, a siRNA molecule, or a piwi-interacting RNA molecule; and more preferably is a transfer RNA molecule. tRNA molecules are highly conserved RNAs with function in various cellular processes such as reverse transcription, porphyrin biosynthesis or the like. In a particular embodiment, the RNA molecule of the invention comprises a sequence selected from SEQ ID NO: 201 to SEQ ID NO: 225 or a functional variant or homologue thereof; or the RNA molecule comprises SEQ ID NO: 201 to SEQ ID NO: 205 or a functional variant or homologue thereof; or the RNA molecule consists of a sequence selected from SEQ ID NO: 201 to SEQ ID NO: 225 or SEQ ID NO: 201 to SEQ ID NO: 205 or a functional variant or homologue thereof.

In an alternative embodiment where the RNA molecule is a small RNA molecule having a sequence length of from about 10 to about 30 base pairs, from about 15 to about 25 base pairs, from about 19 to about 22 base pairs, 19 base pairs or 22 base pairs. The RNA molecule comprises a sequence selected from SEQ ID NO: 1 to SEQ ID NO: 100 or a functional variant or homologue thereof, in particular SEQ ID NO: 1 to SEQ ID NO: 36 or a functional variant or homologue thereof; or consists of a sequence selected from SEQ ID NO: 1 to SEQ ID NO: 100, in particular SEQ ID NO: 1 to SEQ ID NO: 36 or a functional variant or homologue thereof. Preferably, the RNA molecule is a double-stranded RNA molecule having a sense sequence selected from SEQ ID NO: 1 to SEQ ID NO: 100 or a functional variant or homologue thereof, and a complementary antisense sequence. The antisense sequence is complementary to the sense sequence and therefore the antisense sequence is preferably selected from SEQ ID NO: 101 to 200 or functional variant or homologue thereof. In a particular embodiment, the double-stranded RNA molecule of the present invention has a sense sequence selected from SEQ ID NO: 1 to SEQ ID NO: 36 or a functional variant or homologue thereof, and a complementary antisense sequence selected from SEQ ID NO: 101 to SEQ ID NO: 136 or a functional variant or homologue thereof. The inventors unexpectedly found that the double-stranded RNA molecules of the present invention are particularly useful in treatment of cancer such as Taxol-resistant cancer as described in detail below.

The RNA molecule of the present invention is preferably isolated or derived from the plant of the genus *Taxus*. The plant of the genus *Taxus* includes but is not limited to *Taxus baccata, Taxus brevifolia, Taxus chinensis, Taxus chinensis* (Pilger) Rehd. var. *mairei, Taxus yunanensis, Taxus wallischiana, Taxus cuspidate, Taxus sumatrana, Taxus globasa, Taxus canadensis*, and *Taxus floridana*. The plant of the genus *Taxus* may be the source of Taxol. In an embodiment, the RNA molecule is isolated or derived from *Taxus chinensis*.

In more detail, the preferred sequences of the RNA molecules of the present invention are listed in Tables 1 and 2 below. In an embodiment, RNA molecules of SEQ ID NO: 201 to 225 as shown in Table 1 are isolated from a plant of genus *Taxus* in particular from *Taxus chinensis*. These sequences are obtained by extraction, RNA isolation and purification of the plant. The inventors determined these RNA molecules are associated with chloroplasts. One possible approach to obtain the RNA molecules from a particular plant *Taxus chinensis* (Pilger) Rehd. var. *mairei* is illustrated in Example 1. It would be appreciated that other suitable methods for obtaining the isolated and purified RNA molecules of the present invention according to the disclosure herein can be applied, and the methods can be subject to appropriate modification to obtain an improved yield of the RNA molecules, without departing from the scope of the present invention.

TABLE 1

RNA molecules in particular tRNAs isolated from *Taxus chinensis* (Pilger) Rehd. var. mairei according to the present invention.

| SEQ ID NO. | tRNA(s) | Sequence (5' to 3') | Length (mer) |
|---|---|---|---|
| 201 | tRNA$^{His\ (GUG)}$ | GCGGACGUAGCCAAGUGGUCCAAAGGC AGUGGAUUGUGAAUCCACCACGCGCGG GUUCAAUCCCGUCGUUCGCCCA | 78 |
| 202 | tRNA$^{Glu\ (UUC)}$ | GCCCCUAUCGUCUAGUGGCCCAGGACA UCUCUCUUUCAAGGAGGCAACGGGGAU UCGAUUUCCCCUAGGGGUACCA | 76 |
| 203 | tRNA$^{Trp\ (CCA)}$ | GCGCUCUUAGUUCAGUGCGGUAGAACG CAGGUCUCCAAAACCUGAUGCCGUAGG UUCAAAUCCUACAGAGCGCCA | 75 |
| 204 | tRNA$^{Leu\ (CAA)}$ | GCCUUGAUGGUGAAAUGGUAGACACGC GAGACUCAAAAAUCUCGUGCUAAACAGC GUGGAGGUUCGAAUCCUCUUCAAGGCA CCA | 84 |
| 205 | tRNA$^{Arg\ (ACG)}$ | GGGCCUGUAGCUCAGAGGAUUAGAGCA CGUGGUUGCGAACCACGUGUCGGGGG UUCGAAUCCCUCCUCGCCCACCA | 77 |
| 206 | tRNA$^{Asp\ (GUC)}$ | GGGAUUGUAGUUCAAUUGGUUAGAGUA CCGCCCUGUCAAGACGGAAGUUGCGGG UUCGAGCCCCGUCAGUCCCGCCA | 77 |
| 207 | tRNA$^{Asn\ (GUU)}$ | UCCUCAGUAGCUCAGUGGUAGAGCGGU CGGCUGUUAACCGAUUGGUCGUAGGUU CAAAUCCUAUUUGAGGAGCCA | 75 |
| 208 | tRNA$^{Cys\ (GCA)}$ | GGCGACAUAGCCAAGUGGUAAGGCAGG GGACUGCAAAUCCCCAUCCCCAGUUC AAAUCCGGUGUCGCCUCCA | 74 |
| 209 | tRNA$^{Gln\ (UUG)}$ | GGGGCGUGGCCAAGCGGUAAGGCAACA GGUUUUGGUCCUGUUAUUGCGAAGGUU CGAAUCCUUUCGUCCCAGCCA | 75 |
| 210 | tRNA$^{Gly\ (GCC)}$ | GGGUAUUGUUUAAUGGAUAAAAUUUAU UCUUGCCAAGGAUAAGAUGCGGGUUCG AUUCCCGCUACCCGCCCA | 72 |
| 211 | tRNA$^{Ile\ (UAU)}$ | AGGGAUAUAACUCAGUAGUAGAGUGUC ACCUUUAUGUGGUGAAAGUCAUCAGUU CAAACCUGAUUAUCCCUACCA | 75 |
| 212 | tRNA$^{Leu\ (UAG)}$ | GCCGCCAUGGUGAAAUUGGUAGACACG CUGCUCUUAGGAAGCAGUGCUAGAGCA UCUCGGUUCGAAUCCGAGUGGUGGCAC CA | 83 |

TABLE 1-continued

RNA molecules in particular tRNAs isolated from *Taxus chinensis* (Pilger) Rehd. var. mairei according to the present invention.

| SEQ ID NO. | tRNA(s) | Sequence (5' to 3') | Length (mer) |
|---|---|---|---|
| 213 | tRNA$^{Leu\ (UAA)}$ | GGGGAUAUGGCGGAAUUGGUAGACGCU ACGGACUUAAAAAAUCCGUUGGUUUUA UAAACCGUGAGGGUUCAAGUCCCUCUA UCCCCACCA | 90 |
| 214 | tRNA$^{Lys\ (UUU)}$ | GGGUUGUUAACUCAAUGGUAGAGUACU CGGCUUUUAACCGAcGAGUUCCGGGUU CAAGUCCCGGGCAACCCACCA | 75 |
| 215 | tRNA$^{Met\ (CAU)}$ | GCAUCCAUGGCUGAAUGGUCAAAGCAC CCAACUCAUAAUUGGGAAGUCGCGGU UCAAUUCCUGCUGGAUGCACCA | 76 |
| 216 | tRNA$^{Met\ (CAU)}$ | CGCGGAGUAGAGCAGUUUGGUAGCUCG CAAGGCUCAUAACCUUGAAGUCACGGG UUCAAAUCCCGUCUCCGCAACCA | 77 |
| 217 | tRNA$^{Phe\ (GAA)}$ | GUCGGGAUAGCUCAGUUGGUAGAGCAG AGGACUGAAAAUCCUCGUGUCACCAGU UCAAAUCUGGUUCCUGGCACCA | 76 |
| 218 | tRNA$^{Pro\ (UGG)}$ | AGGGAUGUAGCGCAGCUUGGUAGCGCG UUUGUUUUGGGUACAAAAUGUCGCAGG UUCAAAUCCUGUCAUCCCUACCA | 77 |
| 219 | tRNA$^{Pro\ (GGG)}$ | CGGAGCAUAACGCAGUUUGGUAGCGUG CCAUCUUGGGGUGAUGGAGGUCGCGGG UUCAAAUCCUGUUGCUCCGACCA | 77 |
| 220 | tRNA$^{Ser\ (UGA)}$ | GGAGAGAUGGCCGAGUGGUUGAUGGCU CCGGUCUUGAAAACCGGUAUAGUUUUA AAAACUAUCGAGGGUUCGAAUCCCUCU CUCUCCUCCA | 91 |
| 221 | tRNA$^{Ser\ (GCU)}$ | GGAGAGAUGGCUGAGCGGACUAAAGCG GUGGAUUGCUAAUCCGUUGUACAGACU AUCUGUACCGAGGGUUCGAAUCCCUCU UUCUCCGCCA | 91 |
| 222 | tRNA$^{Thr\ (UGU)}$ | GCCUGCUUAGCUCAGAGGUUAGAGCAU CGCACUUGUAAUGCGACGGUCAUCGGU UCGAUCCCGAUAGAAGGCUCCA | 76 |
| 223 | tRNA$^{Thr\ (GGU)}$ | GCACUUUUAACUCAGUGGUAGAGUAAC GCCAUGGUAAGGCGUAAGUCAUCGGUU CAAGCCCGAUAAAGGGCUCCA | 75 |
| 224 | tRNA$^{Tyr\ (GUA)}$ | GGGUCGAUGCCCGAGUGGCUAAUGGGG ACGGACUGUAAAUCCGUUGGCAAUAUG CUUACGCUGGUUCAAAUCCAGCUCGGC CCACCA | 87 |
| 225 | tRNA$^{Arg\ (CUC)}$ | GCGUCCAUCGUCUAAUGGAUAGGACAG AGGUCUUCUAAACCUUAGGUAUAGGUU CAAAUCCUAUUGGACGUACCA | 75 |

The sense sequences of SEQ ID NO: 1 to SEQ ID NO: 100 and the antisense sequences of SEQ ID NO: 101 to SEQ ID NO: 200 as shown in Table 2 are artificially synthesized in accordance with the present invention. In particular, these sequences are derived sequence fragments prepared according to the sequences in Table 1 isolated from *Taxus chinensis* (Pilger) Rehd. var. *mairei*. Each of the sense sequences together with the corresponding antisense sequence form a double-stranded RNA molecule. As shown in Table 2, the sense sequence of SEQ ID NO: 1 and the antisense sequence of SEQ ID NO: 101 form a double-stranded RNA molecule with a length of 22 base pairs, and the resultant RNA molecule is denoted as HC11 for easy reference. Similarly, the sense sequence of SEQ ID NO: 2 and the antisense sequence of SEQ ID NO: 102 form a double-stranded RNA molecule with a length of 19 base pairs, and the resultant RNA molecule is denoted as HC20. Other RNA molecules of the present invention are presented in the Table.

The double-stranded RNA molecules are classified into 2 groups, namely a 5'-terminal group (5'-t), and a 3'-terminal group (3'-t). The 5'-t group RNA molecules contain a 5' terminal portion of the corresponding full-length RNA molecules isolated from the plant; and the 3'-t group RNA molecules contain a 3' terminal portion of the corresponding full-length RNA molecules isolated from the plant. In another embodiment, RNA molecules may contain the anticodon loop portion of the corresponding full-length RNA molecules isolated from the plant and referred as anticodon group RNA molecules. The sense sequences of SEQ ID NO: 1 to SEQ ID NO: 100 can be generated by cleavage at different sites on the full-length RNA molecules SEQ ID NO: 201 to 225.

Further, the RNA molecule of the present invention may comprise a 3' overhang, preferably comprise 2 mer 3' overhangs. The provision of the 3' overhang improves the stability of the RNA molecules.

TABLE 2

RNA molecules derived from the sequences in Table 1 through artificial synthesis according to the present invention.

| Source | Code | SEQ ID NO. | Sense sequence (5' to 3') | SEQ ID NO. | Antisense sequence (5' to 3') | Length (bp) | Group |
|---|---|---|---|---|---|---|---|
| tRNA$^{His\,(GUG)}$ | HC11 | 1 | GCGGACGUAGCCAAGUGGUCCA | 101 | UGGACCACUUGGCUACGUCCGC | 22 | 5'-t |
| | HC20 | 2 | GCGGACGUAGCCAAGUGGU | 102 | ACCACUUGGCUACGUCCGC | 19 | |
| | HC12 | 3 | UCAAUCCCCGUCGUUCGCCCCA | 103 | UGGGGCGAACGACGGGAUUGA | 22 | 3'-t |
| | HC42 | 4 | AUCCCCGUCGUUCGCCCCA | 104 | UGGGGCGAACGACGGGAU | 19 | |
| tRNA$^{Glu\,(UUC)}$ | HC16 | 5 | GCCCCUAUCGUCUAGUGGCCCA | 105 | UGGGCCACUAGACGAUAGGGGC | 22 | 5'-t |
| | HC25 | 6 | GCCCCUAUCGUCUAGUGGC | 106 | GCCACUAGACGAUAGGGGC | 19 | |
| | HC17 | 7 | UCGAUUUCCCCUAGGGGUACCA | 107 | UGGUACCCCUAGGGGAAAUCGA | 22 | 3'-t |
| | HC43 | 8 | AUUUCCCCUAGGGGUACCA | 108 | UGGUACCCCUAGGGGAAAU | 19 | |
| tRNA$^{Trp\,(CCA)}$ | HC30 | 9 | GCGCUCUUAGUUCAGUGCGGUA | 109 | UACCGCACUGAACUAAGAGCGC | 22 | 5'-t |
| | HC23 | 10 | GCGCUCUUAGUUCAGUGCG | 110 | CGCACUGAACUAAGAGCGC | 19 | |
| | HC31 | 11 | GUUCAAAUCCUACAGAGCGCCA | 111 | UGGCGCUCUGUAGGAUUUGAAC | 22 | 3'-t |
| | HC46 | 12 | CAAAUCCUACAGAGCGCCA | 112 | UGGCGCUCUGUAGGAUUUG | 19 | |
| tRNA$^{Leu\,(CAA)}$ | HC18 | 13 | GCCUUGAUGGUGAAAUGGUAGA | 113 | UCUACCAUUUCACCAUCAAGGC | 22 | 5'-t |
| | HC22 | 14 | GCCUUGAUGGUGAAAUGGU | 114 | ACCAUUUCACCAUCAAGGC | 19 | |
| | HC19 | 15 | UCGAAUCCUCUUCAAGGCACCA | 115 | UGGUGCCUUGAAGAGGAUUCGA | 22 | 3'-t |
| | HC44 | 16 | AAUCCUCUUCAAGGCACCA | 116 | UGGUGCCUUGAAGAGGAU U | 19 | |
| tRNA$^{Arg\,(ACG)}$ | HC32 | 17 | GGGCCUGUAGCUCAGAGGAUUA | 117 | UAAUCCUCUGAGCUACAGCCC | 22 | 5'-t |

TABLE 2-continued

RNA molecules derived from the sequences in Table 1 through artificial synthesis according to the present invention.

| Source | Code | SEQ ID NO. | Sense sequence (5' to 3') | SEQ ID NO. | Antisense sequence (5' to 3') | Length (bp) | Group |
|---|---|---|---|---|---|---|---|
| | HC24 | 18 | GGGCCUGUAGCUCAGAGGA | 118 | UCCUCUGAGCUACAGGCC | 19 | |
| | HC33 | 19 | UCGAAUCCCUCCUCGCCCACCA | 119 | UGGUGGGCGAGGAGGGAUUCGA | 22 | 3'-t |
| | HC47 | 20 | AAUCCCUCCUCGCCCACCA | 120 | UGGUGGGCGAGGAGGGAUU | 19 | |
| tRNA<sup>Asp (GUC)</sup> | HC28 | 21 | GGGAUUGUAGUUCAAUUGGUUA | 121 | UAACCAAUUGAACUACAAUCCC | 22 | 5'-t |
| | HC21 | 22 | GGGAUUGUAGUUCAAUUGG | 122 | CCAAUUGAACUACAAUCCC | 19 | |
| | HC29 | 23 | UCGAGCCCCGUCAGUCCCGCCA | 123 | UGGCGGGACUGACGGGGCUCGA | 22 | 3'-t |
| | HC45 | 24 | AGCCCCGUCAGUCCCGCCA | 124 | UGGCGGGACUGACGGGGCU | 19 | |
| tRNA<sup>Cys (GCA)</sup> | HC34 | 25 | GGCGACAUAGCCAAGUGGUAAG | 125 | CUUACCACUUGGCUAUGUCGCC | 22 | 5'-t |
| | HC26 | 26 | GGCGACAUAGCCAAGUGGU | 126 | ACCACUUGGCUAUGUCGCC | 19 | |
| | HC35 | 27 | UCAAAUCCGGGUGUCGCCUCCA | 127 | UGGAGGCGACACCCGGAUUUGA | 22 | 3'-t |
| | HC48 | 28 | AAUCCGGGUGUCGCCUCCA | 128 | UGGAGGCGACACCCGGAUU | 19 | |
| tRNA<sup>Asn (GUU)</sup> | HC36 | 29 | CCUCAGUAGCUCAGUGGUAGAG | 129 | CUCUACCACUGAGCUACUGAGG | 22 | 5'-t |
| | HC27 | 30 | CCUCAGUAGCUCAGUGGUA | 130 | UACCACUGAGCUACUGAGG | 19 | |
| | HC37 | 31 | GGUUCAAAUCCUAUUUGAGGAG | 131 | CUCCUCAAAUAGGAUUUGAACC | 22 | 3'-t |
| | HC49 | 32 | UCAAAUCCUAUUUGAGGAG | 132 | CUCCUCAAAUAGGAUUUGA | 19 | |
| tRNA<sup>Met (CAU)</sup> | HC38 | 33 | CGCGGAGUAGAGCAGUUUGGUA | 133 | UACCAAACUGCUCUACUCCGCG | 22 | 5'-t |
| | HC40 | 34 | CGCGGAGUAGAGCAGUUUG | 134 | CAAACUGCUCUACUCCGCG | 19 | |
| | HC39 | 35 | GGUUCAAAUCCCGUCUCCGCAA | 135 | UUGCGGAGACGGGAUUUGAACC | 22 | 3'-t |
| | HC41 | 36 | UCAAAUCCCGUCUCCGCAA | 136 | UUGCGGAGACGGGAUUUGA | 19 | |
| tRNA<sup>Thr (UGU)</sup> | HC50 | 37 | GCCUGCUUAGCUCAGAGGUUAG | 137 | CUAACCUCUGAGCUAAGCAGGC | 22 | 5'-t |
| | HC52 | 38 | GCCUGCUUAGCUCAGAGGU | 138 | ACCUCUGAGCUAAGCAGGC | 19 | |
| | HC51 | 39 | UCGAUCCCGAUAGAAGGCUCCA | 139 | UGGAGCCUUCUAUCGGGAUCGA | 22 | 3'-t |

TABLE 2-continued

RNA molecules derived from the sequences in Table 1 through artificial synthesis according to the present invention.

| Source | Code | SEQ ID NO. | Sense sequence (5' to 3') | SEQ ID NO. | Antisense sequence (5' to 3') | Length (bp) | Group |
|---|---|---|---|---|---|---|---|
| | HC53 | 40 | AUCCCGAUAGAAGGCUCCA | 140 | UGGAGCCUUCUAUCGGGAU | 19 | |
| tRNA<sup>Pro(UGG)</sup> | HC54 | 41 | AGGGAUGUAGCGCAGCUUGGUA | 141 | UACCAAGCUGCGCUACAUCCCU | 22 | 5'-t |
| | HC56 | 42 | AGGGAUGUAGCGCAGCUUG | 142 | CAAGCUGCGCUACAUCCCU | 19 | |
| | HC55 | 43 | UCAAAUCCUGUCAUCCCUACCA | 143 | UGGUAGGGAUGACAGGAUUUGA | 22 | 3'-t |
| | HC57 | 44 | AAUCCUGUCAUCCCUACCA | 144 | UGGUAGGGAUGACAGGAUU | 19 | |
| tRNA<sup>Gly(GCC)</sup> | HC58 | 45 | GGGUAUUGUUUAAUGGAUAAAA | 145 | UUUUAUCCAUUAAACAAUACCC | 22 | 5'-t |
| | HC60 | 46 | GGGUAUUGUUUAAUGGAUA | 146 | UAUCCAUUAAACAAUACCC | 19 | |
| | HC59 | 47 | UUCGAUUCCCGCUACCCGCCCA | 147 | UGGGCGGGUAGCGGGAAUCGAA | 22 | 3'-t |
| | HC61 | 48 | GAUUCCCGCUACCCGCCCA | 148 | UGGGCGGGUAGCGGGAAUC | 19 | |
| tRNA<sup>Tyr(GUA)</sup> | HC62 | 49 | GGGUCGAUGCCCGAGUGGCUAA | 149 | UUAGCCACUCGGGCAUCGACCC | 22 | 5'-t |
| | HC64 | 50 | GGGUCGAUGCCCGAGUGGC | 150 | GCCACUCGGGCAUCGACCC | 19 | |
| | HC63 | 51 | UCAAAUCCAGCUCGGCCCACCA | 151 | UGGUGGGCCGAGCUGGAUUUGA | 22 | 3'-t |
| | HC65 | 52 | AAUCCAGCUCGGCCCACCA | 152 | UGGUGGGCCGAGCUGGAUU | 19 | |
| tRNA<sup>Leu(UAA)</sup> | HC66 | 53 | GGGGAUAUGGCGGAAUUGGUAG | 153 | CUACCAAUUCCGCCAUAUCCCC | 22 | 5'-t |
| | HC68 | 54 | GGGGAUAUGGCGGAAUUGG | 154 | CCAAUUCCGCCAUAUCCCC | 19 | |
| | HC67 | 55 | UCAAGUCCCUCUAUCCCCACCA | 155 | UGGUGGGGAUAGAGGGACUUGA | 22 | 3'-t |
| | HC69 | 56 | AGUCCCUCUAUCCCCACCA | 156 | UGGUGGGGAUAGAGGGACU | 19 | |
| tRNA<sup>Ser(UGA)</sup> | HC70 | 57 | GGAGAGAUGGCCGAGUGGUUGA | 157 | UCAACCACUCGGCCAUCUCUCC | 22 | 5'-t |
| | HC72 | 58 | GGAGAGAUGGCCGAGUGGU | 158 | ACCACUCGGCCAUCUCUCC | 19 | |
| | HC71 | 59 | UCGAAUCCCUCUCUCUCCUCCA | 159 | UGGAGGAGAGAGAGGGAUUCGA | 22 | 3'-t |
| | HC73 | 60 | AAUCCCUCUCUCUCCUCCA | 160 | UGGAGGAGAGAGAGGGAUU | 19 | |
| tRNA<sup>Gln(UUG)</sup> | HC74 | 61 | GGGGCGUGGCCAAGCGGUAAGG | 161 | CCUUACCGCUUGGCCACGCCCC | 22 | 5'-t |

TABLE 2-continued

RNA molecules derived from the sequences in Table 1 through artificial synthesis according to the present invention.

| Source | Code | SEQ ID NO. | Sense sequence (5' to 3') | SEQ ID NO. | Antisense sequence (5' to 3') | Length (bp) | Group |
|---|---|---|---|---|---|---|---|
| | HC76 | 62 | GGGGCGUGGCCAAGCGGUA | 162 | UACCGCUUGGCCACGCCCC | 19 | |
| | HC75 | 63 | UCGAAUCCUUUCGUCCCAGCCA | 163 | UGGCUGGGACGAAAGGAUUCGA | 22 | 3'-t |
| | HC77 | 64 | AAUCCUUUCGUCCCAGCCA | 164 | UGGCUGGGACGAAAGGAUU | 19 | |
| tRNA$^{Arg(CUC)}$ | HC78 | 65 | GCGUCCAUCGUCUAAUGGAUAG | 165 | CUAUCCAUUAGACGAUGGACGC | 22 | 5'-t |
| | HC80 | 66 | GCGUCCAUCGUCUAAUGGA | 166 | UCCAUUAGACGAUGGACGC | 19 | |
| | HC79 | 67 | UCAAAUCCUAUUGGACGUACCA | 167 | UGGUACGUCCAAUAGGAUUUGA | 22 | 3'-t |
| | HC81 | 68 | AAUCCUAUUGGACGUACCA | 168 | UGGUACGUCCAAUAGGAUU | 19 | |
| tRNA$^{Met(CAU)}$ | HC82 | 69 | GCAUCCAUGGCUGAAUGGUCAA | 169 | UUGACCAUUCAGCCAUGGAUGC | 22 | 5'-t |
| | HC84 | 70 | GCAUCCAUGGCUGAAUGGU | 170 | ACCAUUCAGCCAUGGAUGC | 19 | |
| | HC83 | 71 | UCAAUUCCUGCUGGAUGCACCA | 171 | UGGUGCAUCCAGCAGGAAUUGA | 22 | 3'-t |
| | HC85 | 72 | AUUCCUGCUGGAUGCACCA | 172 | UGGUGCAUCCAGCAGGAAU | 19 | |
| tRNA$^{Leu(UAG)}$ | HC86 | 73 | GCCGCCAUGGUGAAAUUGGUAG | 173 | CUACCAAUUUCACCAUGGCGGC | 22 | 5'-t |
| | HC88 | 74 | GCCGCCAUGGUGAAAUUGG | 174 | CCAAUUUCACCAUGGCGGC | 19 | |
| | HC87 | 75 | UCGAAUCCGAGUGGUGGCACCA | 175 | UGGUGCCACCACUCGGAUUCGA | 22 | 3'-t |
| | HC89 | 76 | AAUCCGAGUGGUGGCACCA | 176 | UGGUGCCACCACUCGGAUU | 19 | |
| tRNA$^{Lys(UUU)}$ | HC90 | 77 | GGGUUGUUAACUCAAUGGUAGA | 177 | UCUACCAUUGAGUUAACACCCC | 22 | 5'-t |
| | HC92 | 78 | GGGUUGUUAACUCAAUGGU | 178 | ACCAUUGAGUUAACAACCC | 19 | |
| | HC91 | 79 | UCAAGUCCCGGGCAACCCACCA | 179 | UGGUGGGUUGCCCGGGACUUGA | 22 | 3'-t |
| | HC93 | 80 | AGUCCCGGGCAACCCACCA | 180 | UGGUGGGUUGCCCGGGACU | 19 | |
| tRNA$^{Phe(GAA)}$ | HC94 | 81 | GUCGGGAUAGCUCAGUUGGUAG | 181 | CUACCAACUGAGCUAUCCCGAC | 22 | 5'-t |
| | HC96 | 82 | GUCGGGAUAGCUCAGUUGG | 182 | CCAACUGAGCUAUCCCGAC | 19 | |
| | HC95 | 83 | UCAAUCUGGUUCCUGGCACCA | 183 | UGGUGCCAGGAACCAGAUUGA | 22 | 3'-t |

TABLE 2-continued

RNA molecules derived from the sequences in Table 1 through artificial synthesis according to the present invention.

| Source | Code | SEQ ID NO. | Sense sequence (5' to 3') | SEQ ID NO. | Antisense sequence (5' to 3') | Length (bp) | Group |
|---|---|---|---|---|---|---|---|
| | HC97 | 84 | AAUCUGGUUCCUGGCACCA | 184 | UGGUGCCAGGAACCAGAUU | 19 | |
| tRNA$^{Pro(GGG)}$ | HC98 | 85 | CGGAGCAUAACGCAGUUUGGUA | 185 | UACCAAACUGCGUUAUGCUCCG | 22 | 5'-t |
| | HC100 | 86 | CGGAGCAUAACGCAGUUUG | 186 | CAAACUGCGUUAUGCUCCG | 19 | |
| | HC99 | 87 | UCAAAUCCUGUUGCUCCGACCA | 187 | UGGUCGGAGCAACAGGAUUUGA | 22 | 3'-t |
| | HC101 | 88 | AAUCCUGUUGCUCCGACCA | 188 | UGGUCGGAGCAACAGGAUU | 19 | |
| tRNA$^{Ser(GCU)}$ | HC102 | 89 | GGAGAGAUGGCUGAGCGGACUA | 189 | UAGUCCGCUCAGCCAUCUCUCC | 22 | 5'-t |
| | HC104 | 90 | GGAGAGAUGGCUGAGCGGA | 190 | UCCGCUCAGCCAUCUCUCC | 19 | |
| | HC103 | 91 | UCGAAUCCCUCUUUCUCCGCCA | 191 | UGGCGGAGAAAGAGGGAUUCGA | 22 | 3'-t |
| | HC105 | 92 | AAUCCCUCUUUCUCCGCCA | 192 | UGGCGGAGAAAGAGGGAUU | 19 | |
| tRNA$^{Thr(GGU)}$ | HC106 | 93 | GCACUUUUAACUCAGUGGUAGA | 193 | UCUACCACUGAGUUAAAAGUGC | 22 | 5'-t |
| | HC108 | 94 | GCACUUUUAACUCAGUGGU | 194 | ACCACUGAGUUAAAAGUGC | 19 | |
| | HC107 | 95 | UCAAGCCCGAUAAAGGGCUCCA | 195 | UGGAGCCCUUUAUCGGGCUUGA | 22 | 3'-t |
| | HC109 | 96 | AGCCCGAUAAAGGGCUCCA | 196 | UGGAGCCCUUUAUCGGGCU | 19 | |
| tRNA$^{Ile(UAU)}$ | HC110 | 97 | AGGGAUAUAACUCAGUAGUAGA | 197 | UCUACUACUGAGUUAUAUCCCU | 22 | 5'-t |
| | HC112 | 98 | AGGGAUAUAACUCAGUAGU | 198 | ACUACUGAGUUAUAUCCCU | 19 | |
| | HC111 | 99 | UCAAACCUGAUUAUCCCUACCA | 199 | UGGUAGGGAUAAUCAGGUUUGA | 22 | 3'-t |
| | HC113 | 100 | AACCUGAUUAUCCCUACCA | 200 | UGGUAGGGAUAAUCAGGUU | 19 | |

The inventors unexpectedly found that the RNA molecules isolated or derived from a plant of genus *Taxus* in particular *Taxus chinensis* (Pilger) Rehd. var. *mairei* are effective against cancer cells, in particular they are capable of inhibiting the growth, proliferation and/or metastasis of cancer cells.

Turning back to the method of treatment, the method comprises the step of administering an effective amount of a RNA molecule as described above to the subject suffering from a cancer. In an embodiment, the step of administering the RNA molecule to the subject comprises contacting cancer cells of the subject with the RNA molecule.

The term "cancer" describes a physiological condition in subjects in which a population of cells are characterized by unregulated malignant (cancerous) cell growth. In an embodiment, the cancer to be treated is ovarian cancer, liver cancer, breast cancer, colorectal cancer, or lung cancer. In a particular embodiment, the cancer is ovarian cancer, colorectal cancer or lung cancer. In an alternative embodiment, the RNA molecules of the present invention are effective in treating cancer which is resistant against currently existing drugs such as Taxol, i.e. can be used to treat cancer which is resistant against Taxol. Specifically, the RNA molecules of the present invention can be used to treat Taxol-resistant lung cancer, Taxol-resistant colorectal cancer or Taxol-resistant ovarian cancer. Accordingly, the method of the present invention can be applied to treat a subject suffering from a multi-drug resistant cancer and related disorders.

The term "subject" used herein refers to a living organism and can include but is not limited to a human and an animal. The subject is preferably a mammal, preferably a human. The RNA molecules may be administered through injection to the subject, preferably a human. The term injection encompasses intravenous, intramuscular, subcutaneous and intradermal administration. In an embodiment, the RNA molecule of the present invention is administered together with suitable excipient(s) to the subject through intravenous injection. For instance, the RNA molecule may be delivered to the subject or cells via transfection, electroporation or viral-mediated delivery.

The expression "effective amount" generally denotes an amount sufficient to produce therapeutically desirable results, wherein the exact nature of the result varies depending on the specific condition which is treated. In this invention, cancer is the condition to be treated and therefore the result is usually an inhibition or suppression of the growth or proliferation of cancer cells, a reduction of cancerous cells or the amelioration of symptoms related to the cancer cells, in particular inhibition of the proliferation of the cancer cells or induction of cell death, i.e. apoptosis of the cancer cells. In an embodiment where the cancer is metastatic cancer, the result is usually an inhibition of migration of cancer cells, suppression of the invasion of cancer cells to other tissues, inhibition of formation metastasis cancer cells at a secondary site distant from the primary site, or amelioration of symptoms related to metastatic cancer.

The effective amount of the RNA molecules of the present invention may depend on the species, body weight, age and individual conditions of the subject and can be determined by standard procedures such as with cell cultures or experimental animals. A dosage of the RNA molecule such as RNA molecule HC11 (formed by SEQ ID NO: 1 and SEQ ID NO: 101) or HC30 (formed by SEQ ID NO: 9 and SEQ ID NO: 109) may, for example, be at least about 0.1 mg/kg to 5 mg/kg, or about 2 mg/kg to 5 mg/kg, in particular 2.4 mg/kg.

The RNA molecule of the present invention may be administered in form of a pharmaceutical composition comprising the RNA molecule and at least one pharmaceutically tolerable excipient. The pharmaceutically tolerable excipient may be one or more of a diluent, a filler, a binder, a disintegrant, a lubricant, a coloring agent, a surfactant, a gene delivery carrier and a preservative. The pharmaceutical composition can be present in solid, semisolid or liquid form, preferably in liquid form. The pharmaceutical composition may comprise further pharmaceutical effective ingredients such as therapeutic compounds which are used for treating cancer such as Taxol. The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

In an embodiment, the RNA molecule is provided in a pharmaceutical composition comprising a gene delivery carrier. The gene delivery carrier refers to any molecules that can act as a carrier for delivering a gene into a cell. In an embodiment where the RNA molecule is transfected into a cell, the gene delivery carrier is considered as a transfecting agent. In an embodiment where the RNA molecule is delivered through a recombinant viral vector, the gene delivery carrier is a viral vector carrying the double-stranded RNA molecule of the present invention. The gene delivery carriers include, but is not limited to, a vector such as a viral vector, a collagen such as atelocollagen, a polymer such as polyethylenimine (PEI), a polypeptide such as poly (L-lysine) and protamine, and a lipid for forming a liposome such as Lipofectamine. The gene delivery carriers may be commercially available such as LipofectamineRNAiMAX Transfection Reagent, Lipofectamine 3000 Reagent, and Lipofectamine® 2000 Transfection Reagent from Thermo Fisher, U.S.A.; RNAi-Mate from GenePharma, China; atelocollagen from Koken Co., Ltd., Japan); and Histidine-Lysine peptide copolymer from siRNAomics, China. The gene delivery carriers may be viral vectors based on retrovirus, adeno-associated virus, adenovirus, and lentivirus. The gene delivery carriers should have a low toxicity and cannot induce significant immune response in the subject. In an embodiment, the RNA molecule is provided in a pharmaceutical composition comprising atelocollagen, wherein atelocollagen forms a complex with the RNA molecule for delivery. In another embodiment, the RNA molecule is provided in a pharmaceutical composition comprising Lipofectamine such as Lipofectamine® RNAiMAX transfection reagent for delivering the RNA molecule to the cells. In a further embodiment, the RNA molecule is inserted into a plasmid and form recombinant vector.

In an embodiment, the pharmaceutical composition may further comprise a nucleic acid stabilizer. The nucleic acid stabilizer refers to any chemicals that are capable of maintaining the stability of the RNA molecule in the composition to minimize or avoid degradation, in particular those having ability to deactivate activity of nucleases or the like degrading the RNA molecules.

Accordingly, the present invention also pertains to a pharmaceutical composition as described above, in particular comprising the RNA molecule and a pharmaceutically tolerable excipient as defined above. In an embodiment, the RNA molecule comprises at least one sequence selected from SEQ ID NO: 1 to 100 or a functional variant or homologue thereof. Preferably, the RNA molecule is isolated or derived from a plant of the genus *Taxus* as described above, in particular from *Taxus chinensis*.

The administration step of the RNA molecule according to the method of the present invention may be performed by injecting a pharmaceutical composition containing the RNA molecule to the target site of the subject, i.e. where cancer cells exist or body tissue adjacent to cancer cells. This is advantageous in that the RNA molecule can be directly delivered to the cancer cells before any cellular degradation such as first pass metabolism.

The RNA molecules of the present invention are also suitable for inhibiting growth or proliferation of cancer cells. In another aspect of the invention, there is provided a method of inhibiting growth or proliferation of cancer cells comprising a step of contacting said cells with an effective amount of a RNA molecule as defined above. Preferably the RNA molecule is isolated or derived from a plant of the genus *Taxus* or comprises a sequence selected from SEQ ID NO: 1 to SEQ ID NO: 100 or a functional variant or homologue thereof. The cancer cells are as defined above. Preferably, the cancer cells are ovarian cancer cells, liver cancer cells, breast cancer cells, colorectal cancer cells, or lung cancer cells. The cancer cells may be resistant against currently existing cancer drugs such as but are not limited to Taxol.

In an embodiment, the RNA molecule has a sequence length of from about 50 to 200 nucleotides, more preferably has a length of from about 60 to about 150 nucleotides, in particular from about 70 to about 100 nucleotides. The RNA molecule is a non-coding molecule preferably a transfer RNA molecule. Preferably, the RNA molecule comprises a sequence selected from SEQ ID NO: 201 to SEQ ID NO: 225 or a functional variant or homologue thereof; or the RNA molecule comprises SEQ ID NO: 201 to SEQ ID NO: 205 or a functional variant or homologue thereof; or the RNA molecule consists of a sequence selected from SEQ ID NO: 201 to SEQ ID NO: 225 or SEQ ID NO: 201 to SEQ ID NO: 205 or a functional variant or homologue thereof.

In an alternative embodiment, the RNA molecule has a sequence length of from about 10 to about 30 base pairs, from about 15 to about 25 base pairs, from about 19 to about 22 base pairs, 19 base pairs or 22 base pairs.

Preferably, the RNA molecule is a double-stranded RNA molecule comprising a sense sequence selected from SEQ ID NO: 1 to SEQ ID NO: 100 or a functional variant or homologue thereof, in particular SEQ ID NO: 1 to SEQ ID NO: 36 or a functional variant or homologue thereof; or consists of a sequence selected from SEQ ID NO: 1 to SEQ ID NO: 100, in particular SEQ ID NO: 1 to SEQ ID NO: 36 or a functional variant or homologue thereof. The double-stranded RNA molecule comprises a complementary anti-sense sequence. The RNA molecule may further comprise 2 mer 3' overhangs.

The step of contacting the cancer cells with the RNA molecule of the present invention may be carried out by applying a composition in particular an incubation solution comprising the RNA molecule to said cancer cells which incubation solution may further comprise suitable excipients as defined above, a buffer or a suitable growth medium. In such embodiment of the present invention, the cancer cells are taken from a subject such as an animal or human, in particular a human. The RNA molecule is provided in the composition at a concentration of at least 3 nM, at least 5 nM, from about 5 nM to about 200 nM, from about 10 nM to about 100 nM, or from about 25 nM to about 50 nM. Further, the excipients may include a gene delivery carrier such as but is not limited to a collagen based carrier or a liposome forming agent. In an embodiment, the collagen based carrier is atelocollagen and the liposome forming agent is Lipofectamine.

In addition to the above, the present invention pertains to a double-stranded RNA molecule as described above, i.e. comprising a sense sequence selected from SEQ ID NO: 1 to SEQ ID NO: 100 or a functional variant or homologue thereof, and a complementary antisense sequence. In particular, the double-stranded RNA molecule consists of a sense sequence selected from SEQ ID NO: 1 to SEQ ID NO: 100 or a functional variant or homologue thereof, a complementary antisense sequence selected from SEQ ID NO: 101 to SEQ ID NO: 200, and optionally a 3' overhang. Example embodiments of the double-stranded RNA molecule are presented in Table 2. The double-stranded RNA may be subject to modification and therefore may carry at least one modified nucleoside selected form inosine, 1-methyladenosine, 2-methyladenosine, $N^6$-methyladenosine, $N^6$-isopentenyladenosine, 2'-O-methyladenosine, $N^6$-acetyladenosine, 1-methylinosine, pseudouridine, dihydrouridine, or 2-methylthio-$N^6$-methyladenosine.

In further aspect of the invention, there is provided a vector comprising a nucleic acid molecule, wherein the nucleic acid molecule is a RNA molecule as described above. In particular, the RNA molecule having a sequence selected from SEQ ID NO: 1 to SEQ ID NO: 100 or a functional variant or homologue thereof. In an embodiment, the vector is a recombinant vector comprising the double-stranded RNA molecule as described above. The vector may be viral-based vector derived from retrovirus, adeno-associated virus, adenovirus, or lentivirus. An ordinary skilled in the art would appreciate suitable approach to incorporate the RNA molecule of the present invention into a vector.

Still further, the present invention pertains to use of a nucleic acid molecule in the preparation of a medicament for treating cancer. The nucleic acid is a RNA molecule as described above including a functional variant or homologue thereof. It would also be appreciated that the RNA molecule of the present invention can be used as a small interfering RNA molecule to interfere the expression of certain genes in the target cancer cells, thereby to cause gene silencing, apoptosis, inhibition of cell growth and proliferation, or the like to achieve the desired therapeutic effect.

Accordingly, the present invention provides a novel and effective approach for treating cancers from various origins by administration of a RNA molecule that is isolated or derived from a plant of the genus *Taxus*, or in particular a RNA molecule comprising a sequence selected from SEQ ID NO: 1 to 100. Administration of said RNA molecule is also suitable for inhibiting growth or proliferation of cancer cells. The RNA molecules are found to be highly effective at inhibiting growth and proliferation of cancer cells in vitro and exhibit an antitumor effect in vivo. Said RNA molecules are also effective against Taxol-resistant cell lines.

The invention is now described in the following non-limiting examples.

EXAMPLES

Chemicals and Materials

Fresh branches of *Taxus chinensis* (Pilger) Rehd. var. *mairei* were collected from Sanming City in the year of 2017 from Fujian Province, China. Cetrimonium bromide (CTAB) and sodium chloride were purchased from-Kingdin Industrial Co., Ltd. (Hong Kong, China). Water-saturated phenol was purchased from Leagene Co., Ltd. (Beijing, China). Chloroform and ethanol were purchased from Anaqua Chemicals Supply Inc. Ltd. (U.S.A.). Isopentanol and guanidinium thiocyanate were purchased from Tokyo Chemical Industry CO., Ltd. (Japan). Tris-HCl and ethylenediaminetetraacetic acid (EDTA) were purchased from Acros Organics (U.S.A), low range ssRNA ladder was purchased from New England Biolabs (Beverly, Mass., U.S.A.). mirVana™ miRNA isolation kit, SYBR gold nucleic acid gel stain and gel loading buffer II were purchased from Thermo Fisher Scientific (U.S.A.). 40% acrylamide/bis solution (19:1), tris/borate/EDTA (TBE), ammonium persulphate (APS) and tetramethylethylenediamine (TEMED) were purchased from Biorad Laboratories Inc. (U.S.A). Taxol-resistance adenocarcinomic human alveolar basal epithelial cell line (A549T) and human ovarian carcinoma cell line (A2780) were purchased from KeyGen Biotech Co. Ltd. (Nanjing, China), human hepatocellular carcinoma cell line (HepG2) and human breast cancer cell line (MCF-7) were purchased from ATCC (Manassas, Va., U.S.A.). Opti-MEM I Reduced Serum Media, Dulbecco's Modified Eagle Medium (DMEM), Minimum Essential Medium (MEM), RPMI Medium 1640, Fetal Bovine Serum (FBS), Penicillin-Streptomycin were purchased from Gibco, (Life Technologies, Auckland, New Zealand). 3-(4,5-Dimethylthiazol-2-yl)-2,5-Diphenyltetrazolium Bromide (MTT) was purchased from Sigma (St. Louis, Mo., U.S.A.).

Example 1

Isolation of RNA Molecules from a Plant of Genus *Taxus*

Branches of *Taxus chinensis* (Pilger) Rehd. var. *mairei* were freshly collected and immediately stored in liquid nitrogen until use. RNAs having a length of 200 nucleotides or below, i.e. small RNAs species, were extracted from *Taxus chinensis* (Pilger) Rehd. var. *mairei* by using an optimized CTAB method combined with a commercial small RNA isolation kit, which method is described by Patel, R. S. et al. in Arch Oral Biol 2011, 56 (12), 1506-1513. Briefly, plant tissues were ground into a fine powder in liquid nitrogen and then homogenized in preheated (65° C.) CTAB extraction buffer using a digital dispersing device (IKA, Germany). After incubation for 2 min at 65° C., the tissue lysate was cooled down immediately in an ice bath for 10 min, followed by centrifugation at 12,000×g for 15 min at 4° C. The supernatant was collected and extracted with an equal volume of phenol:chloroform:isopentanol (50:48:1) by vortexing vigorously. Phases were separated at 4° C. by centrifugation at 12,000×g for 15 min and the supernatant was extracted again as described above with chloroform:isopentanol (24:1). The supernatant was collected and mixed with an equal volume of 6 M guanidinium thiocyanate, followed by adding 100% ethanol to a final concentration of 55%. The mixture was passed through a filter cartridge containing a silica membrane, which immobilizes the RNAs. The filter was then washed for several times with 80% (v/v) ethanol solution, and finally all RNAs were eluted with a low ionic-strength solution or RNase-free water. The small RNA species were isolated and enriched by using a mirVana™ miRNA isolation kit following the manufacturer's instruction.

Figure 1:
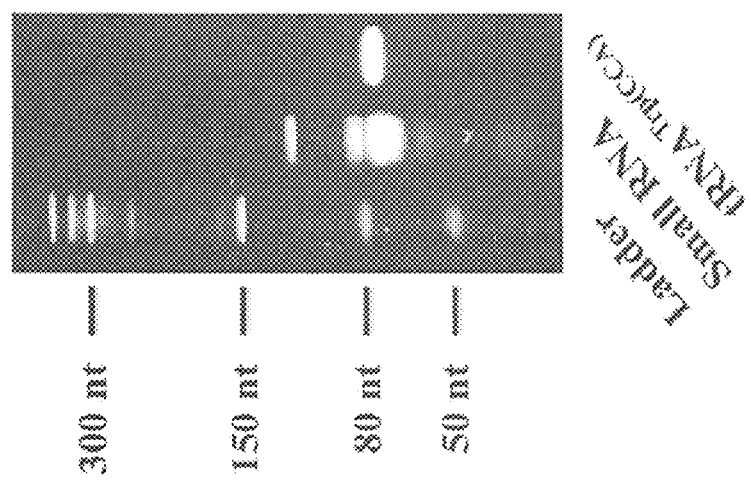
FIG. 1 shows gel electrophoresis profiles of RNA molecules from *Taxus Chinensis* (Pilger) Rehd. var. *mairei*, including low range RNA markers (denoted as "Ladder"), small RNA molecules, and transfer RNA$^{Trp(CCA)}$ in accordance with an example embodiment.

Further, the total tRNAs in the isolated small RNA species were separated by electrophoresis in 6% polyacrylamide TBE gels containing 8 M urea prepared according to the manufacturer's protocol (Biorad, U.S.A.). After staining with SYBR Gold nucleic acid gel stain, polyacrylamide gels were examined using a UV lamp and the region of gels containing total tRNAs were cut off by using a clean and sharp scalpel. FIG. 1 shows gel electrophoresis profiles of small RNA species from *Taxus Chinensis* (Pilger) Rehd. var. *mairei*, including low range RNA markers (denoted as "Ladder"), small RNA species, and transfer RNA$^{TrP(CCA)}$. The band was sliced into small pieces and the total tRNAs were recovered from the gel by electroelution in a 3 kD molecular weight cut-off dialysis tubing (Spectrum, C.A.) at 100 V for 50 min in 1×TAE buffer. The eluents in the dialysis tubing were recovered and the total tRNAs were desalted and concentrated by using the mirVana™ miRNA isolation kit. The quality and purity of the RNA products were then confirmed using a Nanodrop Spectrophotometer (Thermo Scientific, U.S.A.) and Agilent 2100 Bioanalyzer (Agilent, U.S.A.).

The inventors then constructed the total tRNAs library and performed sequencing. Sequencing libraries were generated by using TruSeq small RNA Library Preparation Kit (Illumina, U.S.A.), followed by a round of adaptor ligation, reverse transcription and PCR enrichment. PCR products were then purified and libraries were quantified on the Agilent Bioanalyzer 2100 system (Agilent Technologies, U.S.A.). The library preparations were sequenced at the Novogene Bioinformatics Institute (Beijing, China) on an Illumina HiSeq platform using the 150 bp paired-end (PE150) strategy to generate over 15 million raw paired reads. 1,729,438 clean reads were obtained by removing low quality regions and adaptor sequences. FIG. 2 is a bar chart showing read length distribution of tRNAs. The tRNA genes were identified by using the tRNAscan-SE 2.0 program (http://lowelab.ucsc.edu/tRNAscan-SE/) and annotated by searching the Nucleotide Collection (nr/nt) database using Basic Local Alignment Search Tool (BLAST) program (https://blast.ncbi.nlm.nih.gov/Blast.cgi). 25 tRNA sequences from *Taxus chinensis* (Pilger) Rehd. var. *mairei* were identified and listed in Table 1.

Each of the tRNAs was then isolated from a mixture of small RNAs (<200 mer) from *Taxus chinensis* (Pilger) Rehd. var. *mairei* by immobilization of the target tRNAs onto the streptavidin-coated magnetic beads with specific biotinylated capture DNA probes. To bind specific tRNA molecules, a corresponded single stranded DNA oligonucleotide (20 to 45-mer) were synthesized, which was designed based on the sequence information of Illumina sequencing and should be complementary to a unique segment of the target tRNA. Cognate DNA probes were incubated with small RNA mixture for about 1.5 h in annealing buffer and allowed to hybridize to the targeted tRNA molecules in solution at the proper annealing temperatures that were generally 5° C. lower than the melting temperature (Tm). Streptavidin-coated magnetic beads were then added to the mixture and incubated for 30 min at the annealing temperatures. After the hybridized sequences are immobilized onto the magnetic beads via the streptavidin-biotin bond, the biotinylated DNA/tRNA coated beads were separated with a magnet for 1-2 min and washed 3-4 times in washing buffer at 40° C. The magnetic beads were resuspended to a desired concentration in RNase-free water and thereby to release the immobilized tRNA molecules by incubation at 70° C. for 5 min. Accordingly, the isolated and purified tRNA molecules of SEQ ID NO: 201 to 225 were obtained.

Example 2

Synthesis of RNA Molecules

The inventors designed and synthesized RNA molecules having a length of about 19 to 22 bp based on the 25 isolated tRNA sequences in Example 1. In particular, the tRNA sequences are considered to have at least 3 portions, namely a 5'-terminal portion (5'-t), a 3'-terminal portion (3'-t) and an anticodon portion. Each of the specifically designed RNA molecules contains any one of the portions. For instance, designed RNA molecules containing a 5' terminal portion of the corresponding full-length tRNA sequence are referred as 5'-t group RNA molecules; designed RNA molecules containing a 3' terminal portion of the corresponding full-length tRNA sequence are referred as 3'-t group RNA molecules; designed RNA molecules containing an anticodon portion of the corresponding full-length tRNA sequence are referred as anticodon group RNA molecules. The RNA molecules having a sense sequence selected from SEQ ID NO: 1 to SEQ ID NO: 100 and a complementary antisense sequence selected from SEQ ID NO: 101 to SEQ ID NO: 200, as shown in Table 2, were designed and synthesized by cleavage at different sites on the tRNA sequences in Table 1.

Example 3

Cytotoxic Effect of RNA Molecules on Cancer Cells

A2780, Taxol-resistant A2780, HCT-8, Taxol-resistant HCT-8 and Taxol-resistant A549 cell lines were cultured in RPMI Medium 1640 medium containing 10% FBS and 1% penicillin/streptomycin. HepG2 and MCF-7 cell lines were cultured in Minimum Essential medium containing 10% FBS and 1% penicillin/streptomycin. All cell lines above were cultured at humidified atmosphere containing 5% $CO_2$ at 37° C.

In the cytotoxicity assay, exponentially growing cells of each cancer cell line were plated in 96-well microplate at a density of 5000 cells per well in 100 μL of culture medium and allowed to adhere for 24 h before treatment. Serial concentrations of RNA molecules obtained in Example 1 and 2 in a mixture containing a gene delivery carrier, i.e. Lipofectamine™ RNAiMAX Transfection Reagent (Thermo Fisher Scientific, U.S.A.) were then added to the cells. After treated for 48 h, MTT solution (50 μL per well, 1 mg/mL solution) was added to each well and incubated for 4 h at 37° C. Subsequently, 200 μL dimethyl sulfoxide (DMSO) were added and the optical densities of the resulting solutions were calorimetrically determined at 570 nm using a SpectraMax 190 microplate reader (Molecular Devices, Sunnyvale, Calif., U.S.A). Dose-response curves were obtained, and the $IC_{50}$ values were calculated by GraphPad Prism 5 (GraphPad, La Jolla, Calif., USA). Each experiment was carried out for three times. $IC_{50}$ results were expressed as means±standard deviation.

Figure 3:
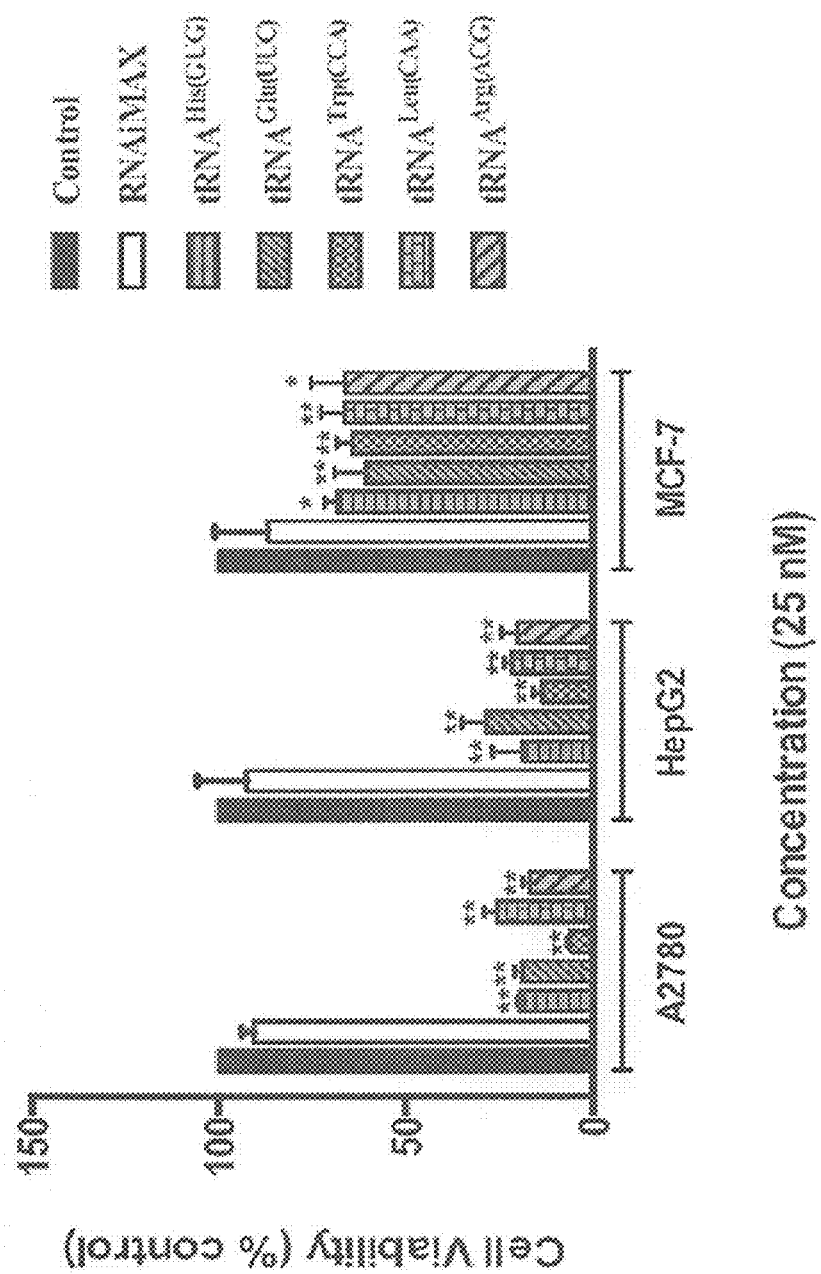
FIG. 3 is a bar chart showing the cytotoxicity of 25 nM RNA molecules tRNA$^{His(GUG)}$, tRNA$^{Glu(UUC)}$, tRNA$^{Trp(CCA)}$, tRNA$^{Leu(CAA)}$, or tRNA$^{Arg(ACG)}$ from *Taxus chinensis* (Pilger) Rehd. var. *mairei* on A2780 cell line, HepG2 cell line, and MCF-7 cell line compared to a control group and a RNAiMAX group where a transfection reagent was added to the cells, in accordance with an example embodiment (mean±SD n=3; *, $p<0.05$, **, $p<0.001$ vs. vehicle control).

With reference to FIG. 3, A2780 cells, HepG2 cells and MCF-7 cells were treated with 25 nM RNA molecules of $tRNA^{His(GUG)}$, $tRNA^{Glu(UUC)}$ $tRNA^{Trp(CCA)}$, $tRNA^{Leu(CAA)}$, $tRNA^{Arg(ACG)}$, i.e. SEQ ID NO: 201 to 205, for 48 h before addition of MTT solution. The cell viability of these cells is compared to a control group and a RNAiMAX group where a transfection reagent was added to the cells. The results show that these RNA molecules are capable of inhibiting the growth and proliferation of ovarian cancer cells, liver cancer cells, and breast cancer cells, whereas the RNA molecules achieve more prominent effect on ovarian and liver cancer cells.

Figures 4A, 4B:
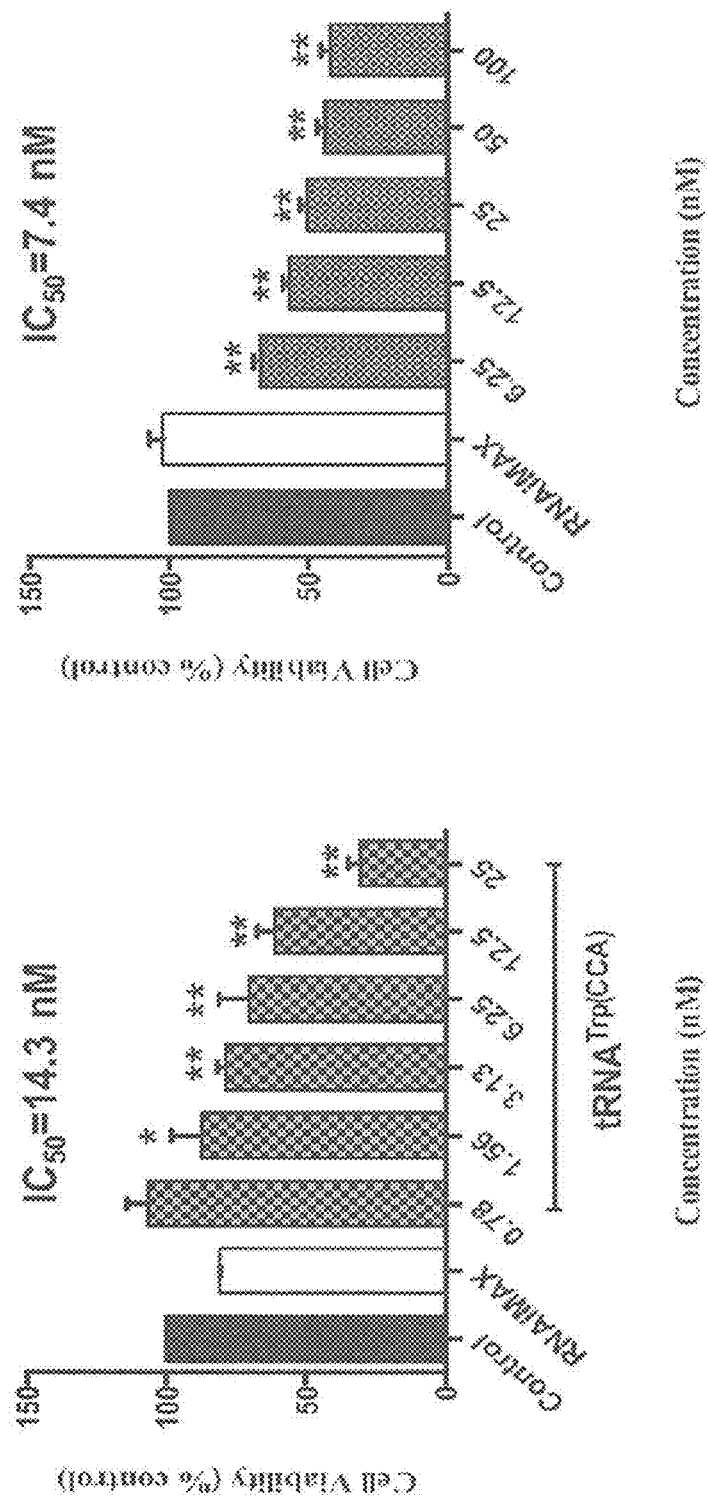
FIG. 4A is a bar chart showing the cell viability of A2780 cells after treatment with a RNA molecule tRNA$^{Trp(CCA)}$ at different concentrations, i.e. 0.78 nM, 1.56 nM, 3.13 nM, 6.25 nM, 12.5 nM and 25 nM, compared to a control group and a RNAiMAX group in accordance with an example embodiment (mean±SD n=3; *, $p<0.05$, **, $p<0.001$ vs. vehicle control).
FIG. 4B is a bar chart showing the cell viability of A2780 cells after treatment with Taxol at different concentrations, i.e. 6.25 nM, 12.5 nM, 25 nM, 50 nM and 100 nM, compared to a control group and a RNAiMAX group in accordance with an example embodiment (mean±SD n=3; *, $p<0.05$, **, $p<0.001$ vs. vehicle control).

FIG. 4A shows the cytotoxic effect of $tRNA^{Trp(CCA)}$, i.e. SEQ ID NO: 203, on A2780 cells. Different concentrations of $tRNA^{Trp(CCA)}$ were used, i.e. 0.78 nM, 1.56 nM, 3.13 nM, 6.25 nM, 12.5 nM and 25 nM, and compared to a control group and a RNAiMAX group. It is shown that the $IC_{50}$ value of $tRNA^{Trp(CCA)}$ on ovarian cells in particular A2780 cells is about 14.3 nM. A comparative example using Taxol was conducted. FIG. 4B show the cytotoxic effect of Taxol on A2780 cells.

Figure 5A:
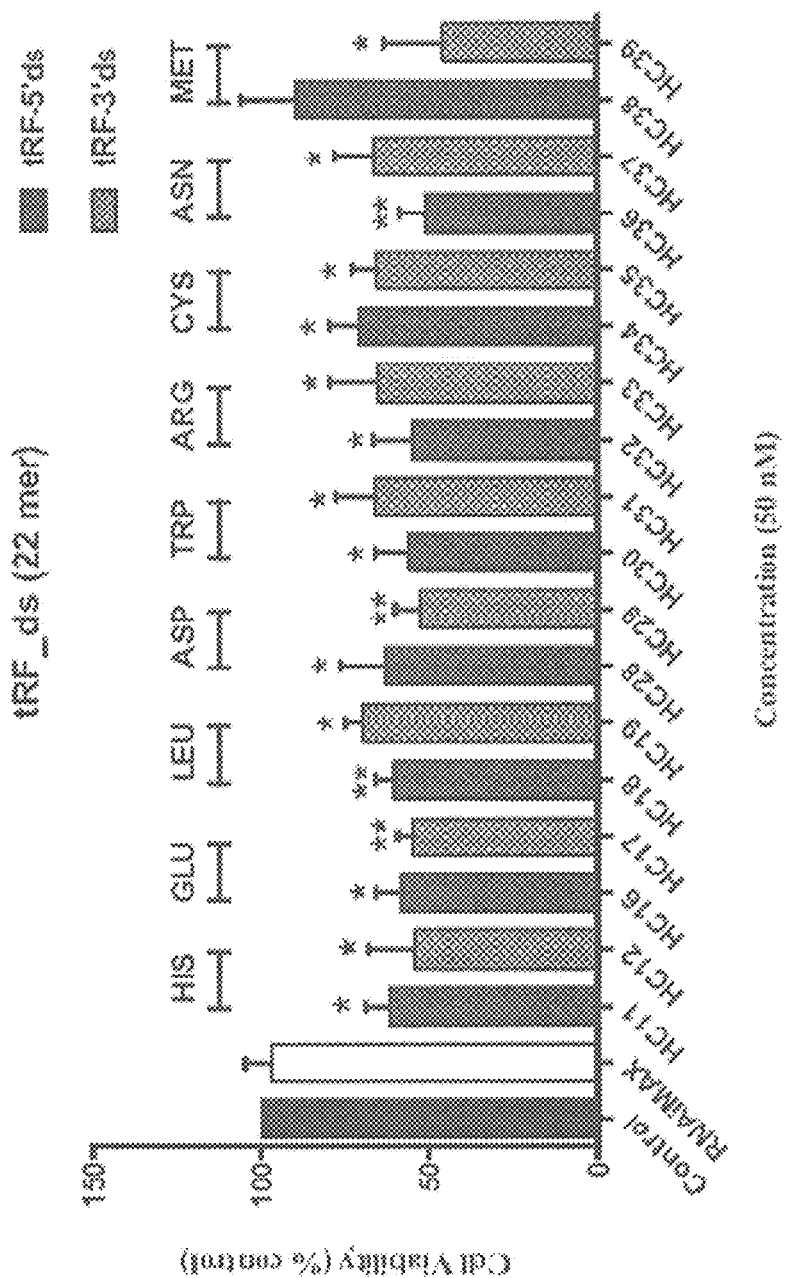
FIG. 5A is a bar chart showing the cell viability of A2780 cells after treatment with different RNA molecules derived from *Taxus Chinensis* (Pilger) Rehd. var. *mairei* with a sequence length of 22 bp at a dose of 50 nM, compared to a control group and a RNAiMAX group in accordance with an example embodiment (mean±SD n=3; *, $p<0.05$, **, $p<0.001$ vs. vehicle control).
Figure 5B:
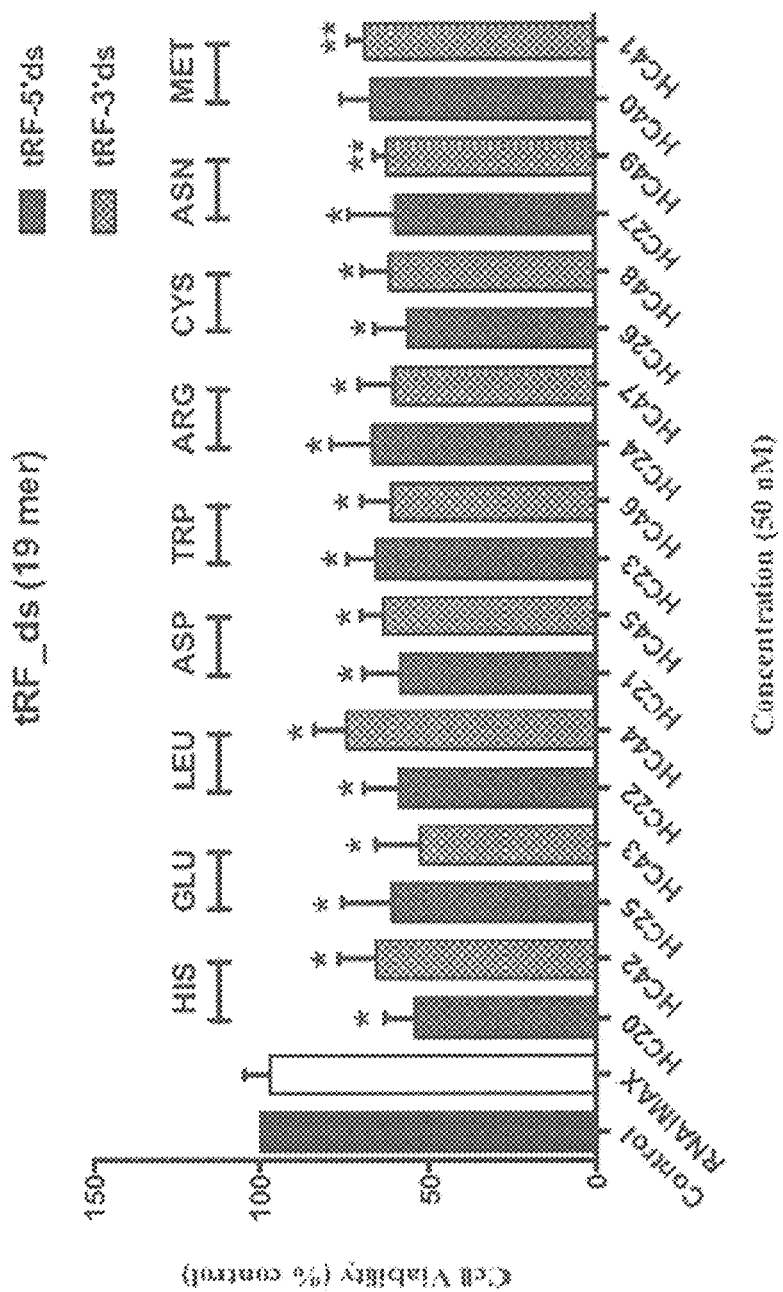
FIG. 5B is a bar chart showing the cell viability of A2780 cells after treatment with different RNA molecules derived from *Taxus Chinensis* (Pilger) Rehd. var. *mairei* with a sequence length of 19 bp at a dose of 50 nM, compared to a control group and a RNAiMAX group in accordance with an example embodiment (mean±SD n=3; *, $p<0.05$, **, $p<0.001$ vs. vehicle control).
Figure 5C:
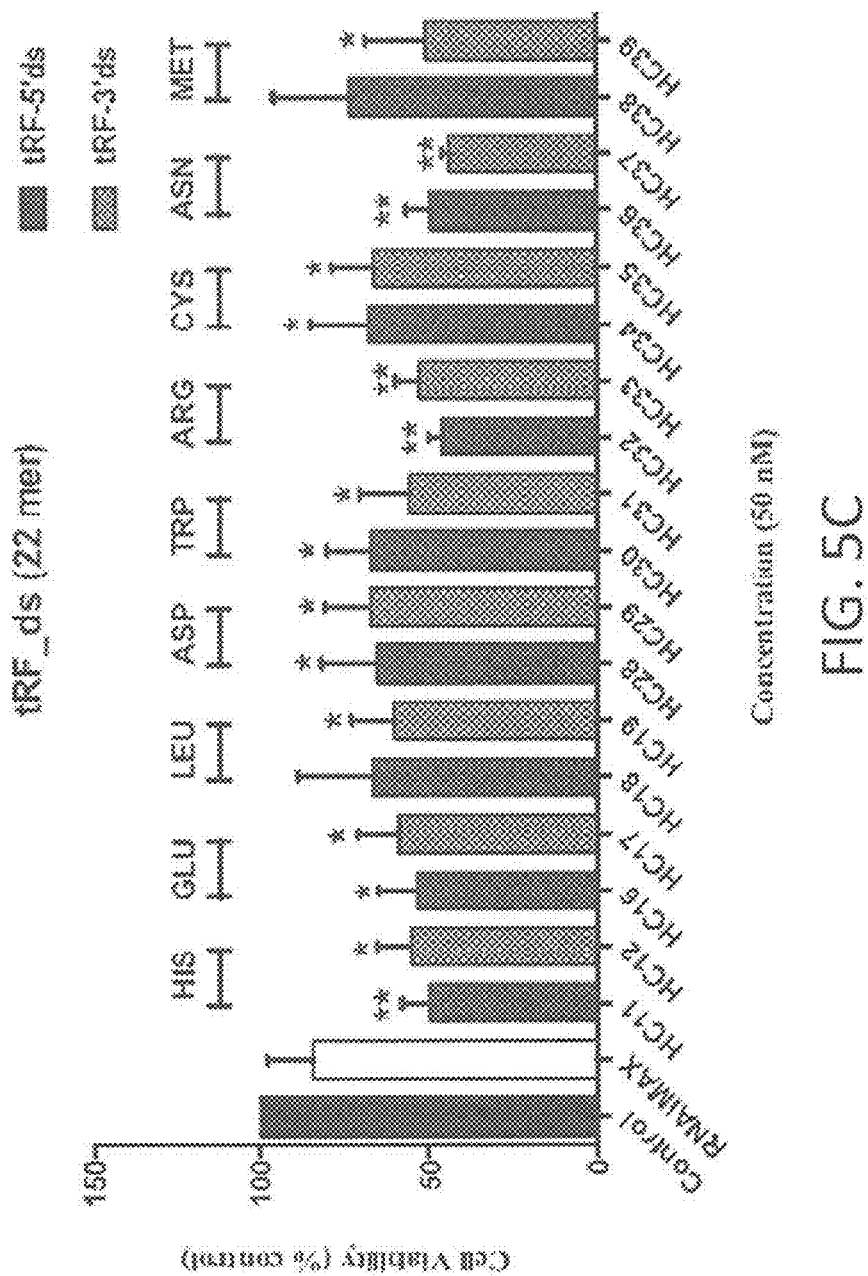
FIG. 5C is a bar chart showing the cell viability of Taxol-resistant A2780 cells (denoted as A2780T cells) after treatment with different RNA molecules derived from *Taxus Chinensis* (Pilger) Rehd. var. *mairei* with a sequence length of 22 bp at a dose of 50 nM, compared to a control group and a RNAiMAX group in accordance with an example embodiment (mean±SD n=3; *, $p<0.05$, **, $p<0.001$ vs. vehicle control).
Figure 5D:
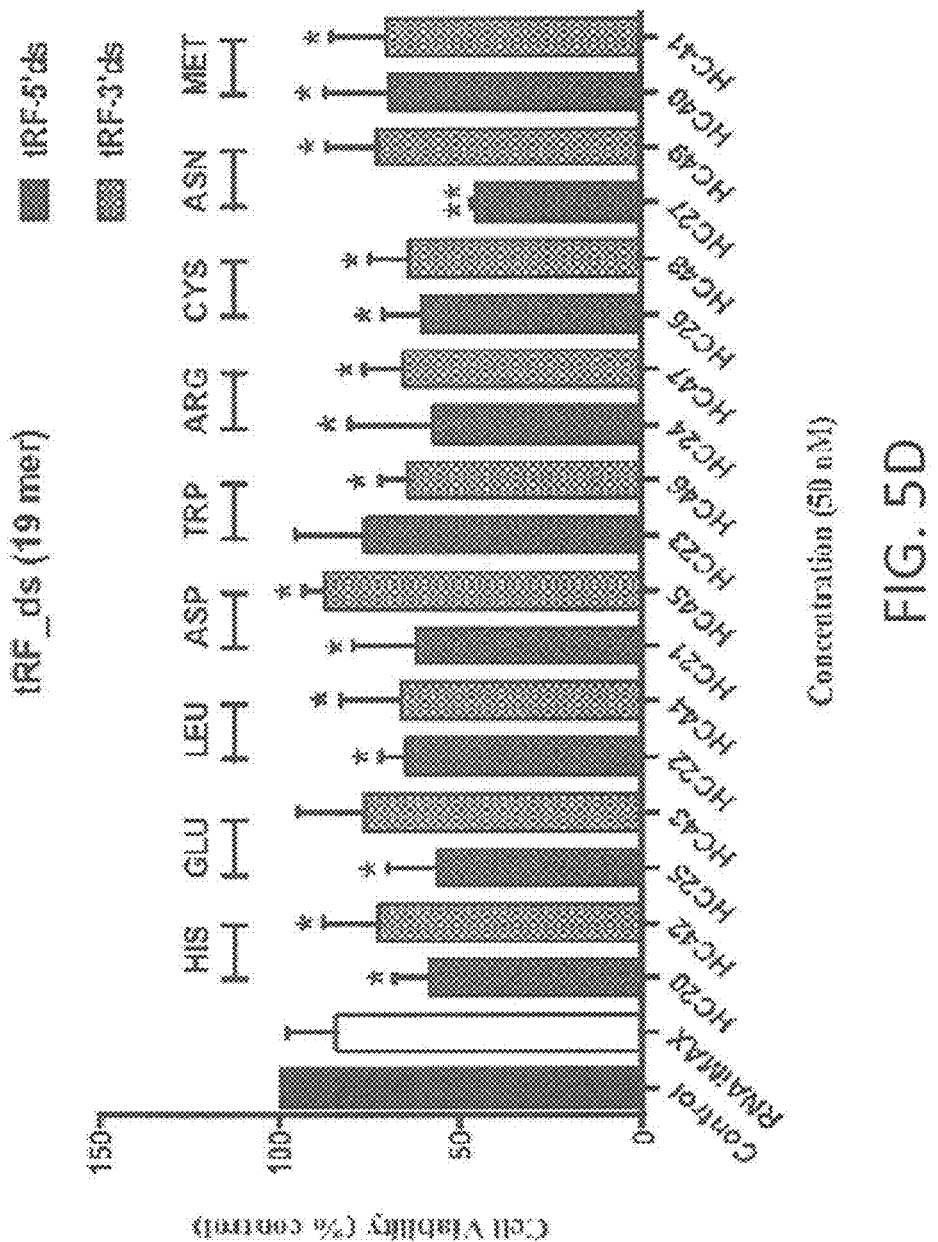
FIG. 5D is a bar chart showing the cell viability of Taxol-resistant A2780T cells after treatment with different RNA molecules derived from *Taxus Chinensis* (Pilger) Rehd. var. *mairei* with a sequence length of 19 bp at a dose of 50 nM, compared to a control group and a RNAiMAX group in accordance with an example embodiment (mean±SD n=3; *, $p<0.05$, **, $p<0.001$ vs. vehicle control).

FIG. 5A and FIG. 5B show the cytotoxic effect of RNA molecules synthesized in Example 2 on A2780 cells, in particular those having sense sequence of SEQ ID NO: 1 to 36. The results show that the RNA molecules designed and synthesized based on the tRNA sequences identified in Example 1 are also effective in inhibiting the growth and proliferation of cancer cells in particular ovarian cancer cells in this example. Further, FIGS. 5C and 5D further demonstrated that the RNA molecules in Example 2 are also capable of inhibiting the growth and/or proliferation of Taxol-resistant A2780 cells. In other words, RNA molecules having sense sequence of SEQ ID NO: 1 to 36 and the complementary antisense sequence are useful in treating cancer which is resistant against Taxol, in particular Taxol-resistant ovarian cancer.

Figure 5E:
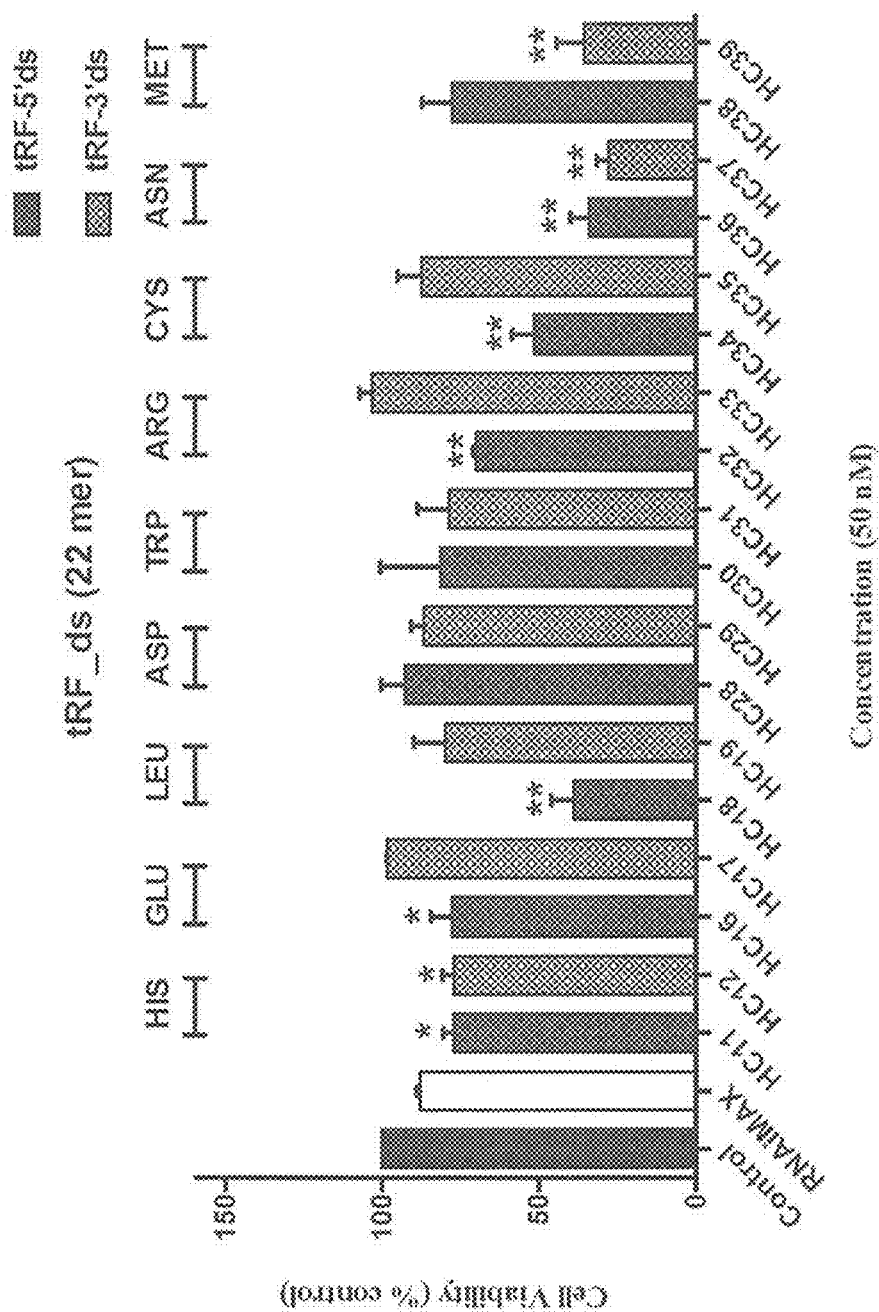
FIG. 5E is a bar chart showing cell viability of HCT-8 cells after treatment with different RNA molecules derived from *Taxus Chinensis* (Pilger) Rehd. var. *mairei* with a sequence length of 22 bp at a dose of 50 nM, compared to a control group and a RNAiMAX group in accordance with an example embodiment (mean±SD n=3; *, $p<0.05$, **, $p<0.001$ vs. vehicle control).
Figure 5F:
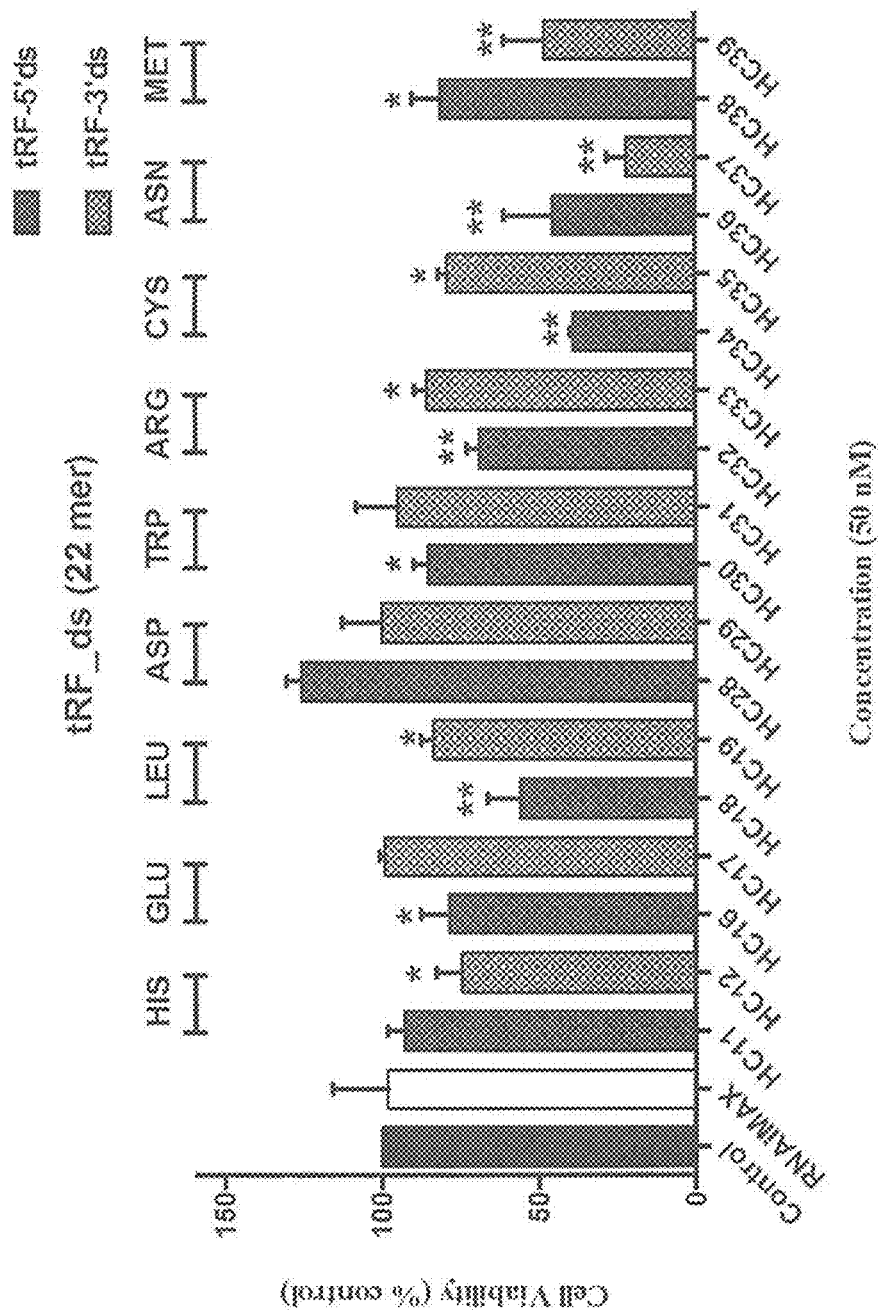
FIG. 5F is a bar chart showing cell viability of Taxol-resistant HCT-8 cells (denoted as HCT-8T cells) after treatment with different RNA molecules derived from *Taxus Chinensis* (Pilger) Rehd. var. *mairei* with a sequence length of 22 bp at a dose of 50 nM, compared to a control group and a RNAiMAX group in accordance with an example embodiment (mean±SD n=3; *, $p<0.05$, **, $p<0.001$ vs. vehicle control).

FIG. 5E show the cytotoxic effect of RNA molecules synthesized in Example 2 on HCT-8 cells, in particular those having a sense sequence of SEQ ID NO: 1 to 36 and a complementary antisense sequence. The results show that these RNA molecules are also effective in inhibiting the growth and proliferation of colorectal cancer cells. Further, FIG. 5F further demonstrated that the RNA molecules in Example 2 are also capable of inhibiting the growth and/or proliferation of Taxol-resistant HCT-8 cells. The results also show that the RNA molecules HC18, HC34, HC36, HC37 and HC39 are useful in treating cancer which is resistant against Taxol, in particular Taxol-resistant colorectal cancer.

Figures 6A, 6B:
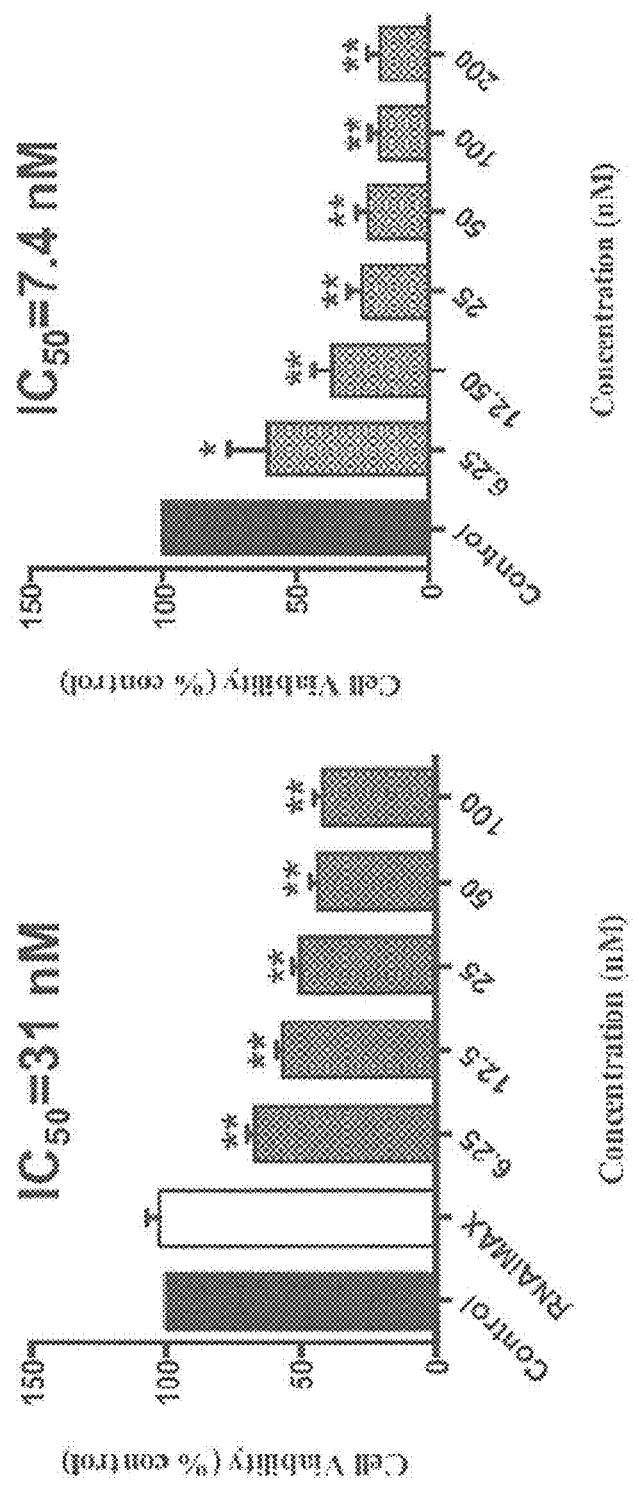
FIG. 6A is a bar chart showing the cell viability of A2780 cells after treatment with RNA molecule HC11 at different concentrations, i.e. 6.25 nM, 12.5 nM, 25 nM, 50 nM and 100 nM, compared to a control group and a RNAiMAX group in accordance with an example embodiment (mean±SD n=3; *, $p<0.05$, **, $p<0.001$ vs. vehicle control).
FIG. 6B is a bar chart showing the cell viability A2780 cells after treatment with Taxol at different concentrations, i.e. 6.25 nM, 12.5 nM, 25 nM, 50 nM, 100 nM and 200 nM, compared to a control group in accordance with an example embodiment (mean±SD n=3; *, $p<0.05$, **, $p<0.001$ vs. vehicle control).

The inventors then specifically determined the cytotoxic effect and $IC_{50}$ of RNA molecule HC11 on A2780 cells, at different concentrations, i.e. 6.25 nM, 12.5 nM, 25 nM, 50 nM and 100 nM. As shown in FIG. 6A, the results are compared to a control group and a RNAiMAX group containing a transfecting agent. The results demonstrated that RNA molecule HC11 has a dose-dependent effect on inhibiting the growth and proliferation of ovarian cancer cells. The $IC_{50}$ of it is 31 nM. A comparative example was conducted using Taxol with results presented in FIG. 6B.

Figures 6C, 6D:
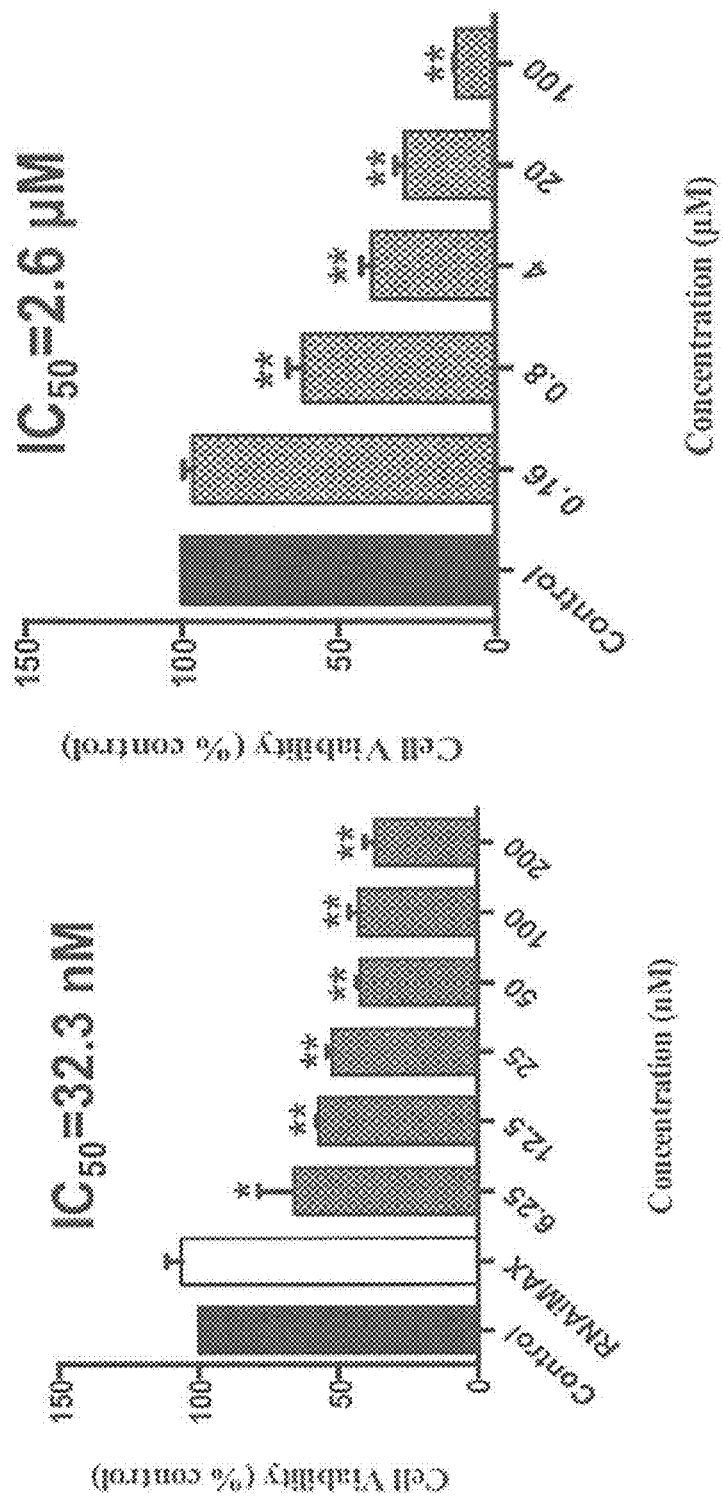
FIG. 6C is a bar chart showing the cell viability of Taxol-resistant A2780T cells after treatment with RNA molecule HC11 at different concentrations, i.e. 6.25 nM, 12.5 nM, 25 nM, 50 nM, 100 nM and 200 nM, compared to a control group and a RNAiMAX group in accordance with an example embodiment (mean±SD n=3; *, $p<0.05$, **, $p<0.001$ vs. vehicle control).
FIG. 6D is a bar chart showing the cell viability of Taxol-resistant A2780T cells after treatment with Taxol at different concentrations, i.e. 0.16 μM, 0.8 μM, 4 μM, 20 μM and 100 μM, compared to a control group in accordance with an example embodiment (mean±SD n=3; *, $p<0.05$, **, $p<0.001$ vs. vehicle control).

Further, the inhibitory effect of HC11 against Taxol-resistant cancer cells was determined. FIG. 6C shows the cell viability of Taxol-resistant A2780T cells after treatment with HC11 at different concentrations, i.e. 6.25 nM, 12.5 nM, 25 nM, 50 nM, 100 nM and 200 nM, compared to a control group and a RNAiMAX group while FIG. 6D shows a comparative example using Taxol in the treatment. The results demonstrated that RNA molecule HC11 has a dose-dependent effect on inhibiting the growth and proliferation of Taxol-resistant ovarian cancer cells and its $IC_{50}$ is 32.3 nM.

Figures 6E, 6F:
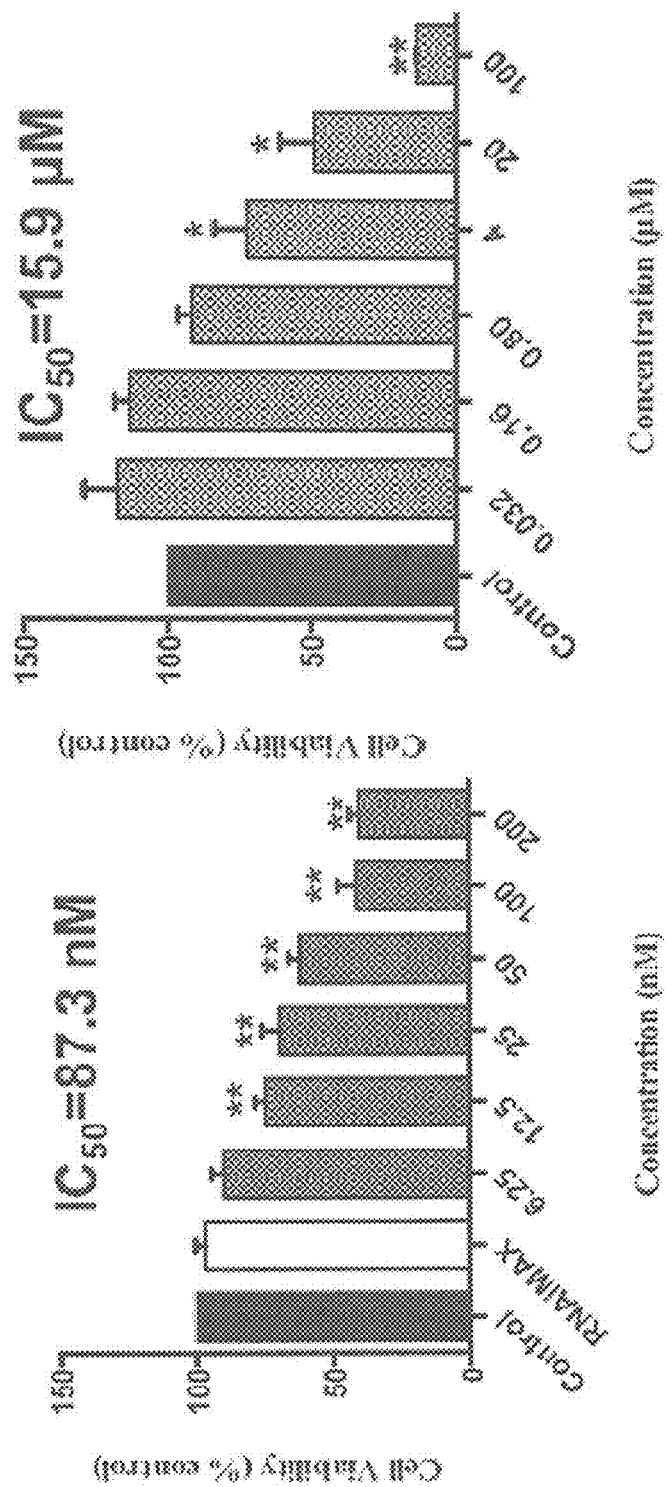
FIG. 6E is a bar chart showing the cell viability of Taxol-resistant A549T cells after treatment with RNA molecule HC11 at different concentrations, i.e. 6.25 nM, 12.5 nM, 25 nM, 50 nM, 100 nM and 200 nM, compared to a control group and a RNAiMAX group in accordance with an example embodiment (mean±SD n=3; *, $p<0.05$, **, $p<0.001$ vs. vehicle control).
FIG. 6F is a bar chart showing the cell viability of Taxol-resistant A549T cells after treatment with Taxol at different concentrations, i.e. 0.032 μM, 0.16 μM, 0.8 μM, 4 μM, 20 μM and 100 μM, compared to a control group in accordance with an example embodiment (mean±SD n=3; *, $p<0.05$, **, $p<0.001$ vs. vehicle control).

Meanwhile, FIG. 6E shows the cell viability of Taxol-resistant A549T cells after treatment with HC11 at different concentrations, and FIG. 6F shows the cell viability of Taxol-resistant A549T cells after treatment with Taxol at different concentrations. The results demonstrated that RNA molecule HC11 has a dose-dependent effect on inhibiting the growth and proliferation of Taxol-resistant lung cancer cells with $IC_{50}$ being 87.3 nM.

Figure 6I:
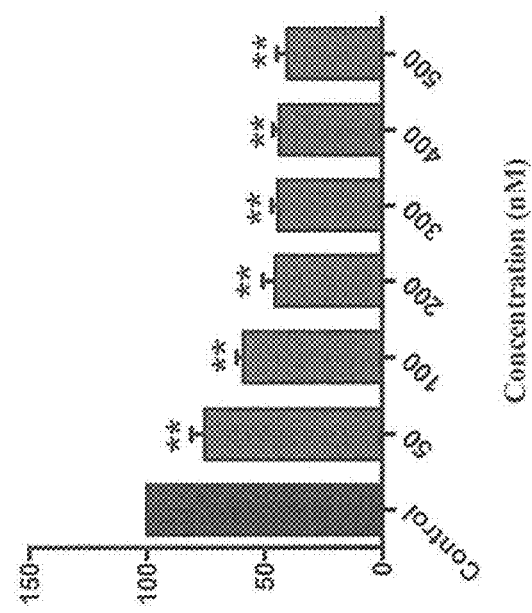
FIG. 6I is a bar chart showing the cell viability of HCT-8 cells after treatment with Taxol at different concentrations, i.e. 50 nM, 100 nM, 200 nM, 300 nM, 400 nM and 500 nM, compared to a control group in accordance with an example embodiment (mean±SD n=3; *, $p<0.05$, **, $p<0.001$ vs. vehicle control).
Figure 6G:
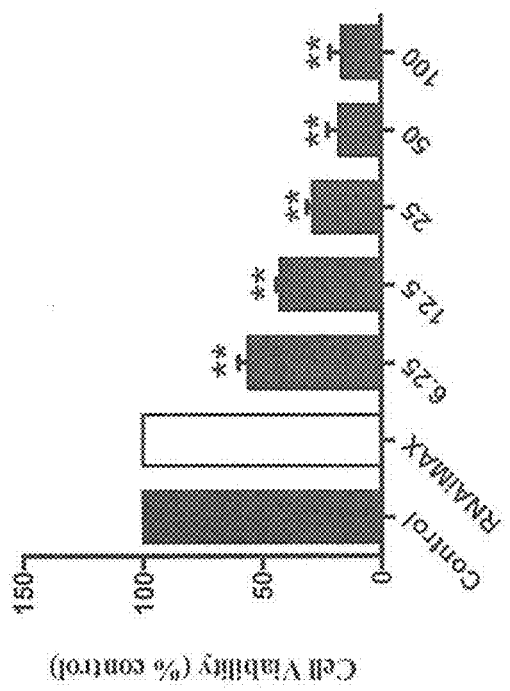
FIG. 6G is a bar chart showing the cell viability of HCT-8 cells after treatment with RNA molecule HC36 at different concentrations, i.e. 6.25 nM, 12.5 nM, 25 nM, 50 nM and 100 nM, compared to a control group and a RNAiMAX group in accordance with an example embodiment (mean±SD n=3; *, $p<0.05$, **, $p<0.001$ vs. vehicle control).
Figure 6H:
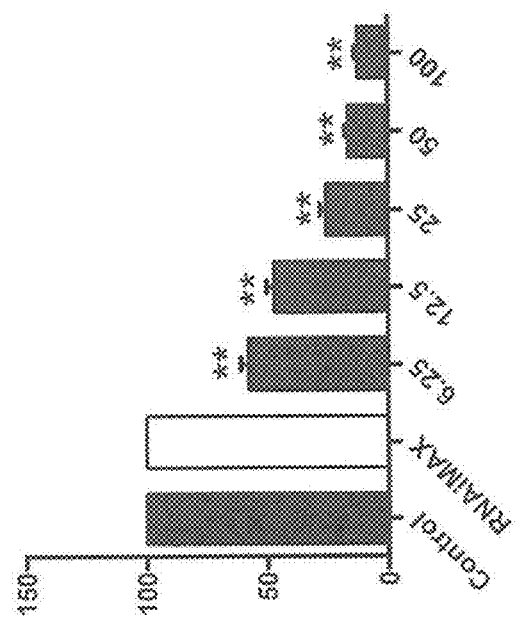
FIG. 6H is a bar chart showing the cell viability of HCT-8 cells after treatment with RNA molecule HC37 at different concentrations, i.e. 6.25 nM, 12.5 nM, 25 nM, 50 nM and 100 nM, compared to a control group and a RNAiMAX group in accordance with an example embodiment (mean±SD n=3; *, $p<0.05$, **, $p<0.001$ vs. vehicle control).

Similarly, the inventors specifically determined the cytotoxic effect and $IC_{50}$ of RNA molecules HC36 and 37 on HCT-8 cells, at different concentrations, i.e. 6.25 nM, 12.5 nM, 25 nM, 50 nM and 100 nM. As shown in FIG. 6G and FIG. 6H, the results are compared to a control group and a RNAiMAX group containing a transfecting agent. The results demonstrated that RNA molecules HC36 and HC37 have dose-dependent effect on inhibiting the growth and proliferation of colorectal cancer cells. The $IC_{50}$ of HC36, 37 is 8.2 and 9.3 nM. A comparative example was conducted using Taxol with results presented in FIG. 6I.

Based on the above results, it is found that the small tRNA molecules isolated or derived from *Taxus chinensis* (Pilger) Rehd. var. *mairei* are highly effective at inhibiting growth and proliferation of cancer cells in vitro. The RNA molecules are also effective against Taxol-resistant cell lines.

Example 4

In Vivo Antitumor Effect of the RNA Molecules

Animal model having xenograft cancer was set. Female BALB/c nude mice (6-8-week old) were purchased from Shanghai SLAC Laboratory Animal Co., Ltd. and maintained at 25° C. with free access to food and water in a special pathogen-free laboratory of the animal environment facilities. The animal experiments were performed in compliance with institutional animal care guidelines and according to committee-approved protocol. To generate tumor xenografts, A2780 cells ($4.0 \times 10^6$) were injected subcutaneously in 100 μL of 1640 medium through a 27-gauge needle into the armpit of 8-week-old BALB/c nude mice. After 4-5 weeks after tumors had reached 60-70 mm³, the tumor-bearing nude mice were treated with synthesized tRF with atelocollagen (Koken Co., Ltd., Tokyo, Japan). The concentration of atelocollagen was 1%, and tumor-adjacent injection was performed by one dose of HC11 or HC30 (RNA molecule of SEQ ID NO: 1 or SEQ ID NO: 9) (GenePharma Co., Ltd., Shanghai, China) at concentration of 2.4 mg/kg with atelocollagen once a week. A control group was set up in which vehicle was administered to the mice. A Taxol group for administering 1 mg/kg Taxol to the mice was also set as a comparison. The entire treatment lasted for 28 days.

Figures 7A, 7B:
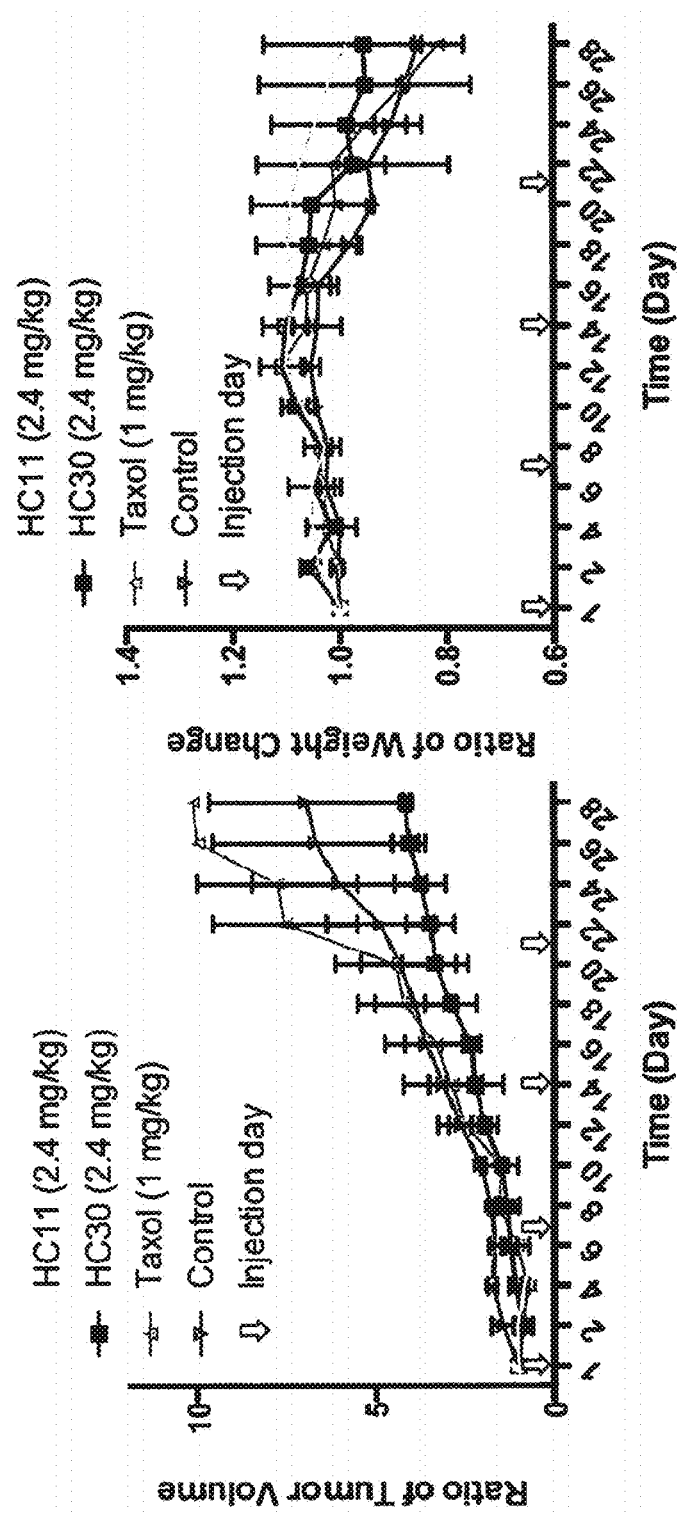
FIG. 7A is a line graph showing the ratio of tumor volume of xenograft implanted A2780 cells in mice over time, in which the mice were treated with RNA molecule HC11 or HC30 with atelocollagen at a dose of 2.4 mg/kg once a week, compared to 1 mg/kg Taxol and a control group.
FIG. 7B is a line graph showing the ratio of weight changes of mice having xenograft implanted A2780 cells, in which the mice were treated with RNA molecule HC11 or HC30 with atelocollagen at a dose of 2.4 mg/kg once a week, compared to 1 mg/kg Taxol and a control group.

Tumor diameters were measured at maximum length and maximum width with digital calipers. And the tumor volume was calculated by the formula: volume=(width)²×length/2. The data were statistically analyzed using GraphPad Prism 5 (GraphPad, La Jolla, Calif., USA). The results are presented in FIGS. 7A and 7B. According to the results, HC11 and HC30 are effective in inhibiting the growth of the tumor inside the mice, and maintaining a relative constant body weight. In other words, the RNA molecules of the present invention are effective in treating cancer cells both in vivo and in vitro.

The invention claimed is:

1. A method of treating a subject suffering from cancer comprising a step of administering an effective amount of a RNA molecule to the subject, wherein the RNA molecule comprises a sense sequence selected from SEQ ID NO: 1 to SEQ ID NO: 100 and a complementary antisense sequence.

2. The method of claim 1, wherein the RNA molecule further comprises 2 mer 3' overhangs.

3. The method of claim 1, wherein the sense sequence is selected from SEQ ID NO: 1 to SEQ ID NO: 36.

4. The method of claim 1, wherein the RNA molecule comprises at least one modified nucleoside selected from inosine, 1-methyladenosine, 2-methyladenosine, $N^6$-m ethyladenosine, $N^6$-isopentenyladenosine, 2'-O-methyladenosine, $N^6$-acetyladenosine, 1-methylinosine, pseudouridine, dihydrouridine, or 2-methylthio-$N^6$-methyladenosine.

5. The method of claim 1, wherein the cancer is ovarian cancer, liver cancer, breast cancer, colorectal cancer, or lung cancer.

6. The method of claim 1, wherein the cancer is resistant against Taxol.

7. The method of claim 1, wherein the RNA molecule is isolated or derived from *Taxus chinensis* (Pilger) Rehd. var. *mairei*.

8. The method of claim 1, wherein the step of administering the RNA molecule to the subject comprises contacting cancer cells of the subject with the RNA molecule.

9. A method of treating a subject suffering from cancer comprising a step of administering an effective amount of a RNA molecule to the subject, wherein the RNA molecule comprises a sequence selected from SEQ ID NO: 201 to SEQ ID NO: 225.

10. A method of inhibiting growth or proliferation of cancer cells comprising a step of contacting said cells with an effective amount of a RNA molecule, wherein the RNA molecule comprises a sense sequence selected from SEQ ID NO: 1 to SEQ ID NO: 100 and a complementary antisense sequence.

11. The method of claim 10, wherein the RNA molecule further comprises 2 mer 3' overhangs.

12. The method of claim 10, wherein the sense sequence is selected from SEQ ID NO: 1 to SEQ ID NO: 36.

13. The method of claim 10, wherein the RNA molecule comprises at least one modified nucleoside selected from inosine, 1-methyladenosine, 2-methyladenosine, $N^6$-methyladenosine, $N^6$-isopentenyladenosine, 2'-O-methyladenosine, acetyladenosine, 1-methylinosine, pseudouridine, dihydrouridine, or 2-methylthio-$N^6$-methyladenosine.

14. The method of claim 10, wherein the cancer cells are ovarian cancer cells, liver cancer cells, breast cancer cells, colorectal cancer cells, or lung cancer cells.

15. The method of claim 10, wherein the cancer cells are resistant against Taxol.

16. The method of claim 10, wherein the RNA molecule is isolated or derived from *Taxus chinensis* (Pilger) Rehd. var. *mairei*.

17. The method of claim 10, wherein the RNA molecule is provided in a composition comprising a gene delivery carrier.

18. A method of inhibiting growth or proliferation of cancer cells comprising a step of contacting said cells with an effective amount of a RNA molecule, wherein the RNA molecule comprises a sequence selected from SEQ ID NO: 201 to SEQ ID NO: 225.

* * * * *

SEQUENCE LISTING

```
<160> NUMBER OF SEQ ID NOS: 225

<210> SEQ ID NO 1
<211> LENGTH: 22
<212> TYPE: RNA
<213> ORGANISM: Artificial Sequence
<220> FEATURE:
<223> OTHER INFORMATION: Synthesized

<400> SEQUENCE: 1
gcggacguag ccaaguggguc ca                                          22

<210> SEQ ID NO 2
<211> LENGTH: 19
<212> TYPE: RNA
<213> ORGANISM: Artificial Sequence
<220> FEATURE:
<223> OTHER INFORMATION: Synthesized

<400> SEQUENCE: 2
gcggacguag ccaaguggu                                               19

<210> SEQ ID NO 3
<211> LENGTH: 22
<212> TYPE: RNA
<213> ORGANISM: Artificial Sequence
<220> FEATURE:
<223> OTHER INFORMATION: Synthesized

<400> SEQUENCE: 3 ucaaucccg ucguucgccc ca                                            22

<210> SEQ ID NO 4
<211> LENGTH: 19
<212> TYPE: RNA
<213> ORGANISM: Artificial Sequence
<220> FEATURE:
<223> OTHER INFORMATION: Synthesized

<400> SEQUENCE: 4
auccccgucg uucgccca                                                19

<210> SEQ ID NO 5
<211> LENGTH: 22
<212> TYPE: RNA
<213> ORGANISM: Artificial Sequence
<220> FEATURE:
<223> OTHER INFORMATION: Synthesized

<400> SEQUENCE: 5
gccccuaucg ucuaguggcc ca                                           22

<210> SEQ ID NO 6
```

```
<211> LENGTH: 19
<212> TYPE: RNA
<213> ORGANISM: Artificial Sequence
<220> FEATURE:
<223> OTHER INFORMATION: Synthesized

<400> SEQUENCE: 6
gccccuaucg ucuaguggc                                                    19

<210> SEQ ID NO 7
<211> LENGTH: 22
<212> TYPE: RNA
<213> ORGANISM: Artificial Sequence
<220> FEATURE:
<223> OTHER INFORMATION: Synthesized

<400> SEQUENCE: 7
ucgauuuccc cuaggguac ca                                                 22

<210> SEQ ID NO 8
<211> LENGTH: 19
<212> TYPE: RNA
<213> ORGANISM: Artificial Sequence
<220> FEATURE:
<223> OTHER INFORMATION: Synthesized

<400> SEQUENCE: 8 auuucccua gggguacca                                                     19

<210> SEQ ID NO 9
<211> LENGTH: 22
<212> TYPE: RNA
<213> ORGANISM: Artificial Sequence
<220> FEATURE:
<223> OTHER INFORMATION: Synthesized

<400> SEQUENCE: 9
gcgcucuuag uucagugcgg ua                                                22

<210> SEQ ID NO 10
<211> LENGTH: 19
<212> TYPE: RNA
<213> ORGANISM: Artificial Sequence
<220> FEATURE:
<223> OTHER INFORMATION: Synthesized

<400> SEQUENCE: 10
gcgcucuuag uucagugcg                                                    19

<210> SEQ ID NO 11
<211> LENGTH: 22
<212> TYPE: RNA
<213> ORGANISM: Artificial Sequence
<220> FEATURE:
<223> OTHER INFORMATION: Synthesized

<400> SEQUENCE: 11
guucaaaucc uacagagcgc ca                                                22

<210> SEQ ID NO 12
<211> LENGTH: 19
<212> TYPE: RNA
<213> ORGANISM: Artificial Sequence
<220> FEATURE:
<223> OTHER INFORMATION: Synthesized

<400> SEQUENCE: 12
```

| | |
|---|---|
| caaauccuac agagcgcca | 19 |

```
<210> SEQ ID NO 13
<211> LENGTH: 22
<212> TYPE: RNA
<213> ORGANISM: Artificial Sequence
<220> FEATURE:
<223> OTHER INFORMATION: Synthesized

<400> SEQUENCE: 13
```

| | |
|---|---|
| gccuugaugg ugaaauggua ga | 22 |

```
<210> SEQ ID NO 14
<211> LENGTH: 19
<212> TYPE: RNA
<213> ORGANISM: Artificial Sequence
<220> FEATURE:
<223> OTHER INFORMATION: Synthesized

<400> SEQUENCE: 14
```

| | |
|---|---|
| gccuugaugg ugaaauggu | 19 |

```
<210> SEQ ID NO 15
<211> LENGTH: 22
<212> TYPE: RNA
<213> ORGANISM: Artificial Sequence
<220> FEATURE:
<223> OTHER INFORMATION: Synthesized

<400> SEQUENCE: 15
```

| | |
|---|---|
| ucgaauccuc uucaaggcac ca | 22 |

```
<210> SEQ ID NO 16
<211> LENGTH: 19
<212> TYPE: RNA
<213> ORGANISM: Artificial Sequence
<220> FEATURE:
<223> OTHER INFORMATION: Synthesized

<400> SEQUENCE: 16
```

| | |
|---|---|
| aauccucuuc aaggcacca | 19 |

```
<210> SEQ ID NO 17
<211> LENGTH: 22
<212> TYPE: RNA
<213> ORGANISM: Artificial Sequence
<220> FEATURE:
<223> OTHER INFORMATION: Synthesized

<400> SEQUENCE: 17
```

| | |
|---|---|
| gggccuguag cucagaggau ua | 22 |

```
<210> SEQ ID NO 18
<211> LENGTH: 19
<212> TYPE: RNA
<213> ORGANISM: Artificial Sequence
<220> FEATURE:
<223> OTHER INFORMATION: Synthesized

<400> SEQUENCE: 18
```

| | |
|---|---|
| gggccuguag cucagagga | 19 |

```
<210> SEQ ID NO 19
<211> LENGTH: 22
<212> TYPE: RNA
```

```
<213> ORGANISM: Artificial Sequence
<220> FEATURE:
<223> OTHER INFORMATION: Synthesized

<400> SEQUENCE: 19
ucgaaucccu ccucgcccac ca                                              22

<210> SEQ ID NO 20
<211> LENGTH: 19
<212> TYPE: RNA
<213> ORGANISM: Artificial Sequence
<220> FEATURE:
<223> OTHER INFORMATION: Synthesized

<400> SEQUENCE: 20
aaucccuccu cgcccacca                                                  19

<210> SEQ ID NO 21
<211> LENGTH: 22
<212> TYPE: RNA
<213> ORGANISM: Artificial Sequence
<220> FEATURE:
<223> OTHER INFORMATION: Synthesized

<400> SEQUENCE: 21
gggauuguag uucaauuggu ua                                              22

<210> SEQ ID NO 22
<211> LENGTH: 19
<212> TYPE: RNA
<213> ORGANISM: Artificial Sequence
<220> FEATURE:
<223> OTHER INFORMATION: Synthesized

<400> SEQUENCE: 22
gggauuguag uucaauugg                                                  19

<210> SEQ ID NO 23
<211> LENGTH: 22
<212> TYPE: RNA
<213> ORGANISM: Artificial Sequence
<220> FEATURE:
<223> OTHER INFORMATION: Synthesized

<400> SEQUENCE: 23
ucgagccccg ucagucccgc ca                                              22

<210> SEQ ID NO 24
<211> LENGTH: 19
<212> TYPE: RNA
<213> ORGANISM: Artificial Sequence
<220> FEATURE:
<223> OTHER INFORMATION: Synthesized

<400> SEQUENCE: 24
agccccguca gucccgcca                                                  19

<210> SEQ ID NO 25
<211> LENGTH: 22
<212> TYPE: RNA
<213> ORGANISM: Artificial Sequence
<220> FEATURE:
<223> OTHER INFORMATION: Synthesized

<400> SEQUENCE: 25
ggcgacauag ccaaguggua ag                                              22
```

<210> SEQ ID NO 26
<211> LENGTH: 19
<212> TYPE: RNA
<213> ORGANISM: Artificial Sequence
<220> FEATURE:
<223> OTHER INFORMATION: Synthesized

<400> SEQUENCE: 26
ggcgacauag ccaaguggu                                              19

<210> SEQ ID NO 27
<211> LENGTH: 22
<212> TYPE: RNA
<213> ORGANISM: Artificial Sequence
<220> FEATURE:
<223> OTHER INFORMATION: Synthesized

<400> SEQUENCE: 27
ucaaauccgg gugucgccuc ca                                          22

<210> SEQ ID NO 28
<211> LENGTH: 19
<212> TYPE: RNA
<213> ORGANISM: Artificial Sequence
<220> FEATURE:
<223> OTHER INFORMATION: Synthesized

<400> SEQUENCE: 28
aauccgggug ucgccucca                                              19

<210> SEQ ID NO 29
<211> LENGTH: 22
<212> TYPE: RNA
<213> ORGANISM: Artificial Sequence
<220> FEATURE:
<223> OTHER INFORMATION: Synthesized

<400> SEQUENCE: 29
ccucaguagc ucagugguag ag                                          22

<210> SEQ ID NO 30
<211> LENGTH: 19
<212> TYPE: RNA
<213> ORGANISM: Artificial Sequence
<220> FEATURE:
<223> OTHER INFORMATION: Synthesized

<400> SEQUENCE: 30
ccucaguagc ucaguggua                                              19

<210> SEQ ID NO 31
<211> LENGTH: 22
<212> TYPE: RNA
<213> ORGANISM: Artificial Sequence
<220> FEATURE:
<223> OTHER INFORMATION: Synthesized

<400> SEQUENCE: 31
gguucaaauc cuauuugagg ag                                          22

<210> SEQ ID NO 32
<211> LENGTH: 19
<212> TYPE: RNA
<213> ORGANISM: Artificial Sequence
<220> FEATURE:

<223> OTHER INFORMATION: Synthesized

<400> SEQUENCE: 32
ucaaauccua uuugaggag                                                  19

<210> SEQ ID NO 33
<211> LENGTH: 22
<212> TYPE: RNA
<213> ORGANISM: Artificial Sequence
<220> FEATURE:
<223> OTHER INFORMATION: Synthesized

<400> SEQUENCE: 33
cgcggaguag agcaguuugg ua                                              22

<210> SEQ ID NO 34
<211> LENGTH: 19
<212> TYPE: RNA
<213> ORGANISM: Artificial Sequence
<220> FEATURE:
<223> OTHER INFORMATION: Synthesized

<400> SEQUENCE: 34
cgcggaguag agcaguuug                                                  19

<210> SEQ ID NO 35
<211> LENGTH: 22
<212> TYPE: RNA
<213> ORGANISM: Artificial Sequence
<220> FEATURE:
<223> OTHER INFORMATION: Synthesized

<400> SEQUENCE: 35
gguucaaauc ccgucuccgc aa                                              22

<210> SEQ ID NO 36
<211> LENGTH: 19
<212> TYPE: RNA
<213> ORGANISM: Artificial Sequence
<220> FEATURE:
<223> OTHER INFORMATION: Synthesized

<400> SEQUENCE: 36
ucaaaucccg ucuccgcaa                                                  19

<210> SEQ ID NO 37
<211> LENGTH: 22
<212> TYPE: RNA
<213> ORGANISM: Artificial Sequence
<220> FEATURE:
<223> OTHER INFORMATION: Synthesized

<400> SEQUENCE: 37
gccugcuuag cucagagguu ag                                              22

<210> SEQ ID NO 38
<211> LENGTH: 19
<212> TYPE: RNA
<213> ORGANISM: Artificial Sequence
<220> FEATURE:
<223> OTHER INFORMATION: Synthesized

<400> SEQUENCE: 38
gccugcuuag cucagaggu                                                  19

<210> SEQ ID NO 39
<211> LENGTH: 22
<212> TYPE: RNA
<213> ORGANISM: Artificial Sequence
<220> FEATURE:
<223> OTHER INFORMATION: Synthesized

<400> SEQUENCE: 39
ucgaucccga uagaaggcuc ca                                              22

<210> SEQ ID NO 40
<211> LENGTH: 19
<212> TYPE: RNA
<213> ORGANISM: Artificial Sequence
<220> FEATURE:
<223> OTHER INFORMATION: Synthesized

<400> SEQUENCE: 40
aucccgauag aaggcucca                                                  19

<210> SEQ ID NO 41
<211> LENGTH: 22
<212> TYPE: RNA
<213> ORGANISM: Artificial Sequence
<220> FEATURE:
<223> OTHER INFORMATION: Synthesized

<400> SEQUENCE: 41
agggauguag cgcagcuugg ua                                              22

<210> SEQ ID NO 42
<211> LENGTH: 19
<212> TYPE: RNA
<213> ORGANISM: Artificial Sequence
<220> FEATURE:
<223> OTHER INFORMATION: Synthesized

<400> SEQUENCE: 42
agggauguag cgcagcuug                                                  19

<210> SEQ ID NO 43
<211> LENGTH: 22
<212> TYPE: RNA
<213> ORGANISM: Artificial Sequence
<220> FEATURE:
<223> OTHER INFORMATION: Synthesized

<400> SEQUENCE: 43
ucaaauccug ucaucccuac ca                                              22

<210> SEQ ID NO 44
<211> LENGTH: 19
<212> TYPE: RNA
<213> ORGANISM: Artificial Sequence
<220> FEATURE:
<223> OTHER INFORMATION: Synthesized

<400> SEQUENCE: 44
aauccuguca ucccuacca                                                  19

<210> SEQ ID NO 45
<211> LENGTH: 22
<212> TYPE: RNA
<213> ORGANISM: Artificial Sequence
<220> FEATURE:
<223> OTHER INFORMATION: Synthesized

```
<400> SEQUENCE: 45
ggguauuguu uaauggauaa aa                                             22

<210> SEQ ID NO 46
<211> LENGTH: 19
<212> TYPE: RNA
<213> ORGANISM: Artificial Sequence
<220> FEATURE:
<223> OTHER INFORMATION: Synthesized

<400> SEQUENCE: 46
ggguauuguu uaauggaua                                                 19

<210> SEQ ID NO 47
<211> LENGTH: 22
<212> TYPE: RNA
<213> ORGANISM: Artificial Sequence
<220> FEATURE:
<223> OTHER INFORMATION: Synthesized

<400> SEQUENCE: 47
uucgauuccc gcuacccgcc ca                                             22

<210> SEQ ID NO 48
<211> LENGTH: 19
<212> TYPE: RNA
<213> ORGANISM: Artificial Sequence
<220> FEATURE:
<223> OTHER INFORMATION: Synthesized

<400> SEQUENCE: 48
gauucccgcu acccgccca                                                 19

<210> SEQ ID NO 49
<211> LENGTH: 22
<212> TYPE: RNA
<213> ORGANISM: Artificial Sequence
<220> FEATURE:
<223> OTHER INFORMATION: Synthesized

<400> SEQUENCE: 49
gggucgaugc ccgaguggcu aa                                             22

<210> SEQ ID NO 50
<211> LENGTH: 19
<212> TYPE: RNA
<213> ORGANISM: Artificial Sequence
<220> FEATURE:
<223> OTHER INFORMATION: Synthesized

<400> SEQUENCE: 50
gggucgaugc ccgaguggc                                                 19

<210> SEQ ID NO 51
<211> LENGTH: 22
<212> TYPE: RNA
<213> ORGANISM: Artificial Sequence
<220> FEATURE:
<223> OTHER INFORMATION: Synthesized

<400> SEQUENCE: 51
ucaaauccag cucggcccac ca                                             22

<210> SEQ ID NO 52
<211> LENGTH: 19
```

```
<212> TYPE: RNA
<213> ORGANISM: Artificial Sequence
<220> FEATURE:
<223> OTHER INFORMATION: Synthesized

<400> SEQUENCE: 52
aauccagcuc ggcccacca                                          19

<210> SEQ ID NO 53
<211> LENGTH: 22
<212> TYPE: RNA
<213> ORGANISM: Artificial Sequence
<220> FEATURE:
<223> OTHER INFORMATION: Synthesized

<400> SEQUENCE: 53
ggggauaugg cggaauuggu ag                                      22

<210> SEQ ID NO 54
<211> LENGTH: 19
<212> TYPE: RNA
<213> ORGANISM: Artificial Sequence
<220> FEATURE:
<223> OTHER INFORMATION: Synthesized

<400> SEQUENCE: 54
ggggauaugg cggaauugg                                          19

<210> SEQ ID NO 55
<211> LENGTH: 22
<212> TYPE: RNA
<213> ORGANISM: Artificial Sequence
<220> FEATURE:
<223> OTHER INFORMATION: Synthesized

<400> SEQUENCE: 55
ucaagucccu cuaucccac ca                                       22

<210> SEQ ID NO 56
<211> LENGTH: 19
<212> TYPE: RNA
<213> ORGANISM: Artificial Sequence
<220> FEATURE:
<223> OTHER INFORMATION: Synthesized

<400> SEQUENCE: 56
agucccucua uccccacca                                          19

<210> SEQ ID NO 57
<211> LENGTH: 22
<212> TYPE: RNA
<213> ORGANISM: Artificial Sequence
<220> FEATURE:
<223> OTHER INFORMATION: Synthesized

<400> SEQUENCE: 57
ggagagaugg ccgagugguu ga                                      22

<210> SEQ ID NO 58
<211> LENGTH: 19
<212> TYPE: RNA
<213> ORGANISM: Artificial Sequence
<220> FEATURE:
<223> OTHER INFORMATION: Synthesized

<400> SEQUENCE: 58
```
ggagagaugg ccgaguggu                               19

<210> SEQ ID NO 59
<211> LENGTH: 22
<212> TYPE: RNA
<213> ORGANISM: Artificial Sequence
<220> FEATURE:
<223> OTHER INFORMATION: Synthesized

<400> SEQUENCE: 59
ucgaaucccu cucucuccuc ca                           22

<210> SEQ ID NO 60
<211> LENGTH: 19
<212> TYPE: RNA
<213> ORGANISM: Artificial Sequence
<220> FEATURE:
<223> OTHER INFORMATION: Synthesized

<400> SEQUENCE: 60
aaucccucuc ucuccucca                               19

<210> SEQ ID NO 61
<211> LENGTH: 22
<212> TYPE: RNA
<213> ORGANISM: Artificial Sequence
<220> FEATURE:
<223> OTHER INFORMATION: Synthesized

<400> SEQUENCE: 61
ggggcguggc caagcgguaa gg                           22

<210> SEQ ID NO 62
<211> LENGTH: 19
<212> TYPE: RNA
<213> ORGANISM: Artificial Sequence
<220> FEATURE:
<223> OTHER INFORMATION: Synthesized

<400> SEQUENCE: 62
ggggcguggc caagcggua                               19

<210> SEQ ID NO 63
<211> LENGTH: 22
<212> TYPE: RNA
<213> ORGANISM: Artificial Sequence
<220> FEATURE:
<223> OTHER INFORMATION: Synthesized

<400> SEQUENCE: 63
ucgaauccuu ucgucccagc ca                           22

<210> SEQ ID NO 64
<211> LENGTH: 19
<212> TYPE: RNA
<213> ORGANISM: Artificial Sequence
<220> FEATURE:
<223> OTHER INFORMATION: Synthesized

<400> SEQUENCE: 64
aauccuuucg ucccagcca                               19

<210> SEQ ID NO 65
<211> LENGTH: 22
<212> TYPE: RNA
<213> ORGANISM: Artificial Sequence

```
<220> FEATURE:
<223> OTHER INFORMATION: Synthesized

<400> SEQUENCE: 65
gcguccaucg ucuaauggau ag                                              22

<210> SEQ ID NO 66
<211> LENGTH: 19
<212> TYPE: RNA
<213> ORGANISM: Artificial Sequence
<220> FEATURE:
<223> OTHER INFORMATION: Synthesized

<400> SEQUENCE: 66
gcguccaucg ucuaaugga                                                  19

<210> SEQ ID NO 67
<211> LENGTH: 22
<212> TYPE: RNA
<213> ORGANISM: Artificial Sequence
<220> FEATURE:
<223> OTHER INFORMATION: Synthesized

<400> SEQUENCE: 67
ucaaauccua uuggacguac ca                                              22

<210> SEQ ID NO 68
<211> LENGTH: 19
<212> TYPE: RNA
<213> ORGANISM: Artificial Sequence
<220> FEATURE:
<223> OTHER INFORMATION: Synthesized

<400> SEQUENCE: 68
aauccuauug gacguacca                                                  19

<210> SEQ ID NO 69
<211> LENGTH: 22
<212> TYPE: RNA
<213> ORGANISM: Artificial Sequence
<220> FEATURE:
<223> OTHER INFORMATION: Synthesized

<400> SEQUENCE: 69
gcauccaugg cugaaugguc aa                                              22

<210> SEQ ID NO 70
<211> LENGTH: 19
<212> TYPE: RNA
<213> ORGANISM: Artificial Sequence
<220> FEATURE:
<223> OTHER INFORMATION: Synthesized

<400> SEQUENCE: 70
gcauccaugg cugaauggu                                                  19

<210> SEQ ID NO 71
<211> LENGTH: 22
<212> TYPE: RNA
<213> ORGANISM: Artificial Sequence
<220> FEATURE:
<223> OTHER INFORMATION: Synthesized

<400> SEQUENCE: 71
ucaauuccug cuggaugcac ca                                              22
```

```
<210> SEQ ID NO 72
<211> LENGTH: 19
<212> TYPE: RNA
<213> ORGANISM: Artificial Sequence
<220> FEATURE:
<223> OTHER INFORMATION: Synthesized

<400> SEQUENCE: 72 auccugcug gaugcacca                                                   19

<210> SEQ ID NO 73
<211> LENGTH: 22
<212> TYPE: RNA
<213> ORGANISM: Artificial Sequence
<220> FEATURE:
<223> OTHER INFORMATION: Synthesized

<400> SEQUENCE: 73
gccgccaugg ugaaauuggu ag                                              22

<210> SEQ ID NO 74
<211> LENGTH: 19
<212> TYPE: RNA
<213> ORGANISM: Artificial Sequence
<220> FEATURE:
<223> OTHER INFORMATION: Synthesized

<400> SEQUENCE: 74
gccgccaugg ugaaauugg                                                  19

<210> SEQ ID NO 75
<211> LENGTH: 22
<212> TYPE: RNA
<213> ORGANISM: Artificial Sequence
<220> FEATURE:
<223> OTHER INFORMATION: Synthesized

<400> SEQUENCE: 75
ucgaauccga gugguggcac ca                                              22

<210> SEQ ID NO 76
<211> LENGTH: 19
<212> TYPE: RNA
<213> ORGANISM: Artificial Sequence
<220> FEATURE:
<223> OTHER INFORMATION: Synthesized

<400> SEQUENCE: 76
aauccgagug guggcacca                                                  19

<210> SEQ ID NO 77
<211> LENGTH: 22
<212> TYPE: RNA
<213> ORGANISM: Artificial Sequence
<220> FEATURE:
<223> OTHER INFORMATION: Synthesized

<400> SEQUENCE: 77
ggguuguuaa cucaauggua ga                                              22

<210> SEQ ID NO 78
<211> LENGTH: 19
<212> TYPE: RNA
<213> ORGANISM: Artificial Sequence
<220> FEATURE:
<223> OTHER INFORMATION: Synthesized
```

-continued

```
<400> SEQUENCE: 78
ggguuguuaa cucaauggu                                              19

<210> SEQ ID NO 79
<211> LENGTH: 22
<212> TYPE: RNA
<213> ORGANISM: Artificial Sequence
<220> FEATURE:
<223> OTHER INFORMATION: Synthesized

<400> SEQUENCE: 79
ucaagucccg ggcaacccac ca                                          22

<210> SEQ ID NO 80
<211> LENGTH: 19
<212> TYPE: RNA
<213> ORGANISM: Artificial Sequence
<220> FEATURE:
<223> OTHER INFORMATION: Synthesized

<400> SEQUENCE: 80
agucccgggc aacccacca                                              19

<210> SEQ ID NO 81
<211> LENGTH: 22
<212> TYPE: RNA
<213> ORGANISM: Artificial Sequence
<220> FEATURE:
<223> OTHER INFORMATION: Synthesized

<400> SEQUENCE: 81
gucgggauag cucaguuggu ag                                          22

<210> SEQ ID NO 82
<211> LENGTH: 19
<212> TYPE: RNA
<213> ORGANISM: Artificial Sequence
<220> FEATURE:
<223> OTHER INFORMATION: Synthesized

<400> SEQUENCE: 82
gucgggauag cucaguugg                                              19

<210> SEQ ID NO 83
<211> LENGTH: 22
<212> TYPE: RNA
<213> ORGANISM: Artificial Sequence
<220> FEATURE:
<223> OTHER INFORMATION: Synthesized

<400> SEQUENCE: 83
ucaaaucugg uuccuggcac ca                                          22

<210> SEQ ID NO 84
<211> LENGTH: 19
<212> TYPE: RNA
<213> ORGANISM: Artificial Sequence
<220> FEATURE:
<223> OTHER INFORMATION: Synthesized

<400> SEQUENCE: 84
aaucugguuc cuggcacca                                              19

<210> SEQ ID NO 85
```

```
<211> LENGTH: 22
<212> TYPE: RNA
<213> ORGANISM: Artificial Sequence
<220> FEATURE:
<223> OTHER INFORMATION: Synthesized

<400> SEQUENCE: 85
cggagcauaa cgcaguuugg ua                                               22

<210> SEQ ID NO 86
<211> LENGTH: 19
<212> TYPE: RNA
<213> ORGANISM: Artificial Sequence
<220> FEATURE:
<223> OTHER INFORMATION: Synthesized

<400> SEQUENCE: 86
cggagcauaa cgcaguuug                                                   19

<210> SEQ ID NO 87
<211> LENGTH: 22
<212> TYPE: RNA
<213> ORGANISM: Artificial Sequence
<220> FEATURE:
<223> OTHER INFORMATION: Synthesized

<400> SEQUENCE: 87
ucaaauccug uugcuccgac ca                                               22

<210> SEQ ID NO 88
<211> LENGTH: 19
<212> TYPE: RNA
<213> ORGANISM: Artificial Sequence
<220> FEATURE:
<223> OTHER INFORMATION: Synthesized

<400> SEQUENCE: 88
aauccuguug cuccgacca                                                   19

<210> SEQ ID NO 89
<211> LENGTH: 22
<212> TYPE: RNA
<213> ORGANISM: Artificial Sequence
<220> FEATURE:
<223> OTHER INFORMATION: Synthesized

<400> SEQUENCE: 89
ggagagaugg cugagcggac ua                                               22

<210> SEQ ID NO 90
<211> LENGTH: 19
<212> TYPE: RNA
<213> ORGANISM: Artificial Sequence
<220> FEATURE:
<223> OTHER INFORMATION: Synthesized

<400> SEQUENCE: 90
ggagagaugg cugagcgga                                                   19

<210> SEQ ID NO 91
<211> LENGTH: 22
<212> TYPE: RNA
<213> ORGANISM: Artificial Sequence
<220> FEATURE:
<223> OTHER INFORMATION: Synthesized

<400> SEQUENCE: 91
```
ucgaaucccu cuuucuccgc ca                                          22

<210> SEQ ID NO 92
<211> LENGTH: 19
<212> TYPE: RNA
<213> ORGANISM: Artificial Sequence
<220> FEATURE:
<223> OTHER INFORMATION: Synthesized

<400> SEQUENCE: 92 aauccccucuu ucuccgcca                                             19

<210> SEQ ID NO 93
<211> LENGTH: 22
<212> TYPE: RNA
<213> ORGANISM: Artificial Sequence
<220> FEATURE:
<223> OTHER INFORMATION: Synthesized

<400> SEQUENCE: 93
gcacuuuuaa cucaguggua ga                                          22

<210> SEQ ID NO 94
<211> LENGTH: 19
<212> TYPE: RNA
<213> ORGANISM: Artificial Sequence
<220> FEATURE:
<223> OTHER INFORMATION: Synthesized

<400> SEQUENCE: 94
gcacuuuuaa cucaguggu                                              19

<210> SEQ ID NO 95
<211> LENGTH: 22
<212> TYPE: RNA
<213> ORGANISM: Artificial Sequence
<220> FEATURE:
<223> OTHER INFORMATION: Synthesized

<400> SEQUENCE: 95
ucaagcccga uaaagggcuc ca                                          22

<210> SEQ ID NO 96
<211> LENGTH: 19
<212> TYPE: RNA
<213> ORGANISM: Artificial Sequence
<220> FEATURE:
<223> OTHER INFORMATION: Synthesized

<400> SEQUENCE: 96
agcccgauaa agggcucca                                              19

<210> SEQ ID NO 97
<211> LENGTH: 22
<212> TYPE: RNA
<213> ORGANISM: Artificial Sequence
<220> FEATURE:
<223> OTHER INFORMATION: Synthesized

<400> SEQUENCE: 97
agggauauaa cucaguagua ga                                          22

<210> SEQ ID NO 98
<211> LENGTH: 19
<212> TYPE: RNA

```
<213> ORGANISM: Artificial Sequence
<220> FEATURE:
<223> OTHER INFORMATION: Synthesized

<400> SEQUENCE: 98
agggauauaa cucaguagu                                                    19

<210> SEQ ID NO 99
<211> LENGTH: 22
<212> TYPE: RNA
<213> ORGANISM: Artificial Sequence
<220> FEATURE:
<223> OTHER INFORMATION: Synthesized

<400> SEQUENCE: 99
ucaaaccuga uuaucccuac ca                                                22

<210> SEQ ID NO 100
<211> LENGTH: 19
<212> TYPE: RNA
<213> ORGANISM: Artificial Sequence
<220> FEATURE:
<223> OTHER INFORMATION: Synthesized

<400> SEQUENCE: 100
aaccugauua ucccuacca                                                    19

<210> SEQ ID NO 101
<211> LENGTH: 22
<212> TYPE: RNA
<213> ORGANISM: Artificial Sequence
<220> FEATURE:
<223> OTHER INFORMATION: Synthesized

<400> SEQUENCE: 101
uggaccacuu ggcuacgucc gc                                                22

<210> SEQ ID NO 102
<211> LENGTH: 19
<212> TYPE: RNA
<213> ORGANISM: Artificial Sequence
<220> FEATURE:
<223> OTHER INFORMATION: Synthesized

<400> SEQUENCE: 102
accacuuggc uacguccgc                                                    19

<210> SEQ ID NO 103
<211> LENGTH: 22
<212> TYPE: RNA
<213> ORGANISM: Artificial Sequence
<220> FEATURE:
<223> OTHER INFORMATION: Synthesized

<400> SEQUENCE: 103
uggggcgaac gacggggauu ga                                                22

<210> SEQ ID NO 104
<211> LENGTH: 19
<212> TYPE: RNA
<213> ORGANISM: Artificial Sequence
<220> FEATURE:
<223> OTHER INFORMATION: Synthesized

<400> SEQUENCE: 104
uggggcgaac gacggggau                                                    19
```

<210> SEQ ID NO 105
<211> LENGTH: 22
<212> TYPE: RNA
<213> ORGANISM: Artificial Sequence
<220> FEATURE:
<223> OTHER INFORMATION: Synthesized

<400> SEQUENCE: 105
ugggccacua gacgauaggg gc                                              22

<210> SEQ ID NO 106
<211> LENGTH: 19
<212> TYPE: RNA
<213> ORGANISM: Artificial Sequence
<220> FEATURE:
<223> OTHER INFORMATION: Synthesized

<400> SEQUENCE: 106
gccacuagac gauaggggc                                                  19

<210> SEQ ID NO 107
<211> LENGTH: 22
<212> TYPE: RNA
<213> ORGANISM: Artificial Sequence
<220> FEATURE:
<223> OTHER INFORMATION: Synthesized

<400> SEQUENCE: 107
ugguaccccu aggggaaauc ga                                              22

<210> SEQ ID NO 108
<211> LENGTH: 19
<212> TYPE: RNA
<213> ORGANISM: Artificial Sequence
<220> FEATURE:
<223> OTHER INFORMATION: Synthesized

<400> SEQUENCE: 108
ugguaccccu aggggaaau                                                  19

<210> SEQ ID NO 109
<211> LENGTH: 22
<212> TYPE: RNA
<213> ORGANISM: Artificial Sequence
<220> FEATURE:
<223> OTHER INFORMATION: Synthesized

<400> SEQUENCE: 109
uaccgcacug aacuaagagc gc                                              22

<210> SEQ ID NO 110
<211> LENGTH: 19
<212> TYPE: RNA
<213> ORGANISM: Artificial Sequence
<220> FEATURE:
<223> OTHER INFORMATION: Synthesized

<400> SEQUENCE: 110
cgcacugaac uaagagcgc                                                  19

<210> SEQ ID NO 111
<211> LENGTH: 22
<212> TYPE: RNA
<213> ORGANISM: Artificial Sequence
<220> FEATURE:

```
<223> OTHER INFORMATION: Synthesized

<400> SEQUENCE: 111
uggcgcucug uaggauuuga ac                                              22

<210> SEQ ID NO 112
<211> LENGTH: 19
<212> TYPE: RNA
<213> ORGANISM: Artificial Sequence
<220> FEATURE:
<223> OTHER INFORMATION: Synthesized

<400> SEQUENCE: 112
uggcgcucug uaggauuug                                                  19

<210> SEQ ID NO 113
<211> LENGTH: 22
<212> TYPE: RNA
<213> ORGANISM: Artificial Sequence
<220> FEATURE:
<223> OTHER INFORMATION: Synthesized

<400> SEQUENCE: 113
ucuaccauuu caccaucaag gc                                              22

<210> SEQ ID NO 114
<211> LENGTH: 19
<212> TYPE: RNA
<213> ORGANISM: Artificial Sequence
<220> FEATURE:
<223> OTHER INFORMATION: Synthesized

<400> SEQUENCE: 114
accauuucac caucaaggc                                                  19

<210> SEQ ID NO 115
<211> LENGTH: 22
<212> TYPE: RNA
<213> ORGANISM: Artificial Sequence
<220> FEATURE:
<223> OTHER INFORMATION: Synthesized

<400> SEQUENCE: 115
uggugccuug aagaggauuc ga                                              22

<210> SEQ ID NO 116
<211> LENGTH: 19
<212> TYPE: RNA
<213> ORGANISM: Artificial Sequence
<220> FEATURE:
<223> OTHER INFORMATION: Synthesized

<400> SEQUENCE: 116
uggugccuug aagaggauu                                                  19

<210> SEQ ID NO 117
<211> LENGTH: 22
<212> TYPE: RNA
<213> ORGANISM: Artificial Sequence
<220> FEATURE:
<223> OTHER INFORMATION: Synthesized

<400> SEQUENCE: 117
uaauccucug agcuacaggc cc                                              22
```

<210> SEQ ID NO 118
<211> LENGTH: 19
<212> TYPE: RNA
<213> ORGANISM: Artificial Sequence
<220> FEATURE:
<223> OTHER INFORMATION: Synthesized

<400> SEQUENCE: 118
uccucugagc uacaggccc                                                    19

<210> SEQ ID NO 119
<211> LENGTH: 22
<212> TYPE: RNA
<213> ORGANISM: Artificial Sequence
<220> FEATURE:
<223> OTHER INFORMATION: Synthesized

<400> SEQUENCE: 119 ugguggcga ggagggauuc ga                                                 22

<210> SEQ ID NO 120
<211> LENGTH: 19
<212> TYPE: RNA
<213> ORGANISM: Artificial Sequence
<220> FEATURE:
<223> OTHER INFORMATION: Synthesized

<400> SEQUENCE: 120 ugguggcga ggagggauu                                                     19

<210> SEQ ID NO 121
<211> LENGTH: 22
<212> TYPE: RNA
<213> ORGANISM: Artificial Sequence
<220> FEATURE:
<223> OTHER INFORMATION: Synthesized

<400> SEQUENCE: 121
uaaccaauug aacuacaauc cc                                                22

<210> SEQ ID NO 122
<211> LENGTH: 19
<212> TYPE: RNA
<213> ORGANISM: Artificial Sequence
<220> FEATURE:
<223> OTHER INFORMATION: Synthesized

<400> SEQUENCE: 122
ccaauugaac uacaauccc                                                    19

<210> SEQ ID NO 123
<211> LENGTH: 22
<212> TYPE: RNA
<213> ORGANISM: Artificial Sequence
<220> FEATURE:
<223> OTHER INFORMATION: Synthesized

<400> SEQUENCE: 123
uggcgggacu gacggggcuc ga                                                22

<210> SEQ ID NO 124
<211> LENGTH: 19
<212> TYPE: RNA
<213> ORGANISM: Artificial Sequence
<220> FEATURE:
<223> OTHER INFORMATION: Synthesized

```
<400> SEQUENCE: 124
uggcgggacu gacggggcu                                              19

<210> SEQ ID NO 125
<211> LENGTH: 22
<212> TYPE: RNA
<213> ORGANISM: Artificial Sequence
<220> FEATURE:
<223> OTHER INFORMATION: Synthesized

<400> SEQUENCE: 125
cuuaccacuu ggcuaugucg cc                                          22

<210> SEQ ID NO 126
<211> LENGTH: 19
<212> TYPE: RNA
<213> ORGANISM: Artificial Sequence
<220> FEATURE:
<223> OTHER INFORMATION: Synthesized

<400> SEQUENCE: 126
accacuuggc uaugucgcc                                              19

<210> SEQ ID NO 127
<211> LENGTH: 22
<212> TYPE: RNA
<213> ORGANISM: Artificial Sequence
<220> FEATURE:
<223> OTHER INFORMATION: Synthesized

<400> SEQUENCE: 127
uggaggcgac acccggauuu ga                                          22

<210> SEQ ID NO 128
<211> LENGTH: 19
<212> TYPE: RNA
<213> ORGANISM: Artificial Sequence
<220> FEATURE:
<223> OTHER INFORMATION: Synthesized

<400> SEQUENCE: 128
uggaggcgac acccggauu                                              19

<210> SEQ ID NO 129
<211> LENGTH: 22
<212> TYPE: RNA
<213> ORGANISM: Artificial Sequence
<220> FEATURE:
<223> OTHER INFORMATION: Synthesized

<400> SEQUENCE: 129
cucuaccacu gagcuacuga gg                                          22

<210> SEQ ID NO 130
<211> LENGTH: 19
<212> TYPE: RNA
<213> ORGANISM: Artificial Sequence
<220> FEATURE:
<223> OTHER INFORMATION: Synthesized

<400> SEQUENCE: 130
uaccacugag cuacugagg                                              19

<210> SEQ ID NO 131
<211> LENGTH: 22
```

```
<212> TYPE: RNA
<213> ORGANISM: Artificial Sequence
<220> FEATURE:
<223> OTHER INFORMATION: Synthesized

<400> SEQUENCE: 131
cuccucaaau aggauuugaa cc                                          22

<210> SEQ ID NO 132
<211> LENGTH: 19
<212> TYPE: RNA
<213> ORGANISM: Artificial Sequence
<220> FEATURE:
<223> OTHER INFORMATION: Synthesized

<400> SEQUENCE: 132
cuccucaaau aggauuuga                                              19

<210> SEQ ID NO 133
<211> LENGTH: 22
<212> TYPE: RNA
<213> ORGANISM: Artificial Sequence
<220> FEATURE:
<223> OTHER INFORMATION: Synthesized

<400> SEQUENCE: 133
uaccaaacug cucuacuccg cg                                          22

<210> SEQ ID NO 134
<211> LENGTH: 19
<212> TYPE: RNA
<213> ORGANISM: Artificial Sequence
<220> FEATURE:
<223> OTHER INFORMATION: Synthesized

<400> SEQUENCE: 134
caaacugcuc uacuccgcg                                              19

<210> SEQ ID NO 135
<211> LENGTH: 22
<212> TYPE: RNA
<213> ORGANISM: Artificial Sequence
<220> FEATURE:
<223> OTHER INFORMATION: Synthesized

<400> SEQUENCE: 135
uugcggagac gggauuugaa cc                                          22

<210> SEQ ID NO 136
<211> LENGTH: 19
<212> TYPE: RNA
<213> ORGANISM: Artificial Sequence
<220> FEATURE:
<223> OTHER INFORMATION: Synthesized

<400> SEQUENCE: 136
uugcggagac gggauuuga                                              19

<210> SEQ ID NO 137
<211> LENGTH: 22
<212> TYPE: RNA
<213> ORGANISM: Artificial Sequence
<220> FEATURE:
<223> OTHER INFORMATION: Synthesized

<400> SEQUENCE: 137
```
cuaaccucug agcuaagcag gc                                               22

<210> SEQ ID NO 138
<211> LENGTH: 19
<212> TYPE: RNA
<213> ORGANISM: Artificial Sequence
<220> FEATURE:
<223> OTHER INFORMATION: Synthesized

<400> SEQUENCE: 138
accucugagc uaagcaggc                                                   19

<210> SEQ ID NO 139
<211> LENGTH: 22
<212> TYPE: RNA
<213> ORGANISM: Artificial Sequence
<220> FEATURE:
<223> OTHER INFORMATION: Synthesized

<400> SEQUENCE: 139
uggagccuuc uaucgggauc ga                                               22

<210> SEQ ID NO 140
<211> LENGTH: 19
<212> TYPE: RNA
<213> ORGANISM: Artificial Sequence
<220> FEATURE:
<223> OTHER INFORMATION: Synthesized

<400> SEQUENCE: 140
uggagccuuc uaucgggau                                                   19

<210> SEQ ID NO 141
<211> LENGTH: 22
<212> TYPE: RNA
<213> ORGANISM: Artificial Sequence
<220> FEATURE:
<223> OTHER INFORMATION: Synthesized

<400> SEQUENCE: 141
uaccaagcug cgcuacaucc cu                                               22

<210> SEQ ID NO 142
<211> LENGTH: 19
<212> TYPE: RNA
<213> ORGANISM: Artificial Sequence
<220> FEATURE:
<223> OTHER INFORMATION: Synthesized

<400> SEQUENCE: 142
caagcugcgc uacaucccu                                                   19

<210> SEQ ID NO 143
<211> LENGTH: 22
<212> TYPE: RNA
<213> ORGANISM: Artificial Sequence
<220> FEATURE:
<223> OTHER INFORMATION: Synthesized

<400> SEQUENCE: 143
ugguagggau gacaggauuu ga                                               22

<210> SEQ ID NO 144
<211> LENGTH: 19
<212> TYPE: RNA
<213> ORGANISM: Artificial Sequence

```
<220> FEATURE:
<223> OTHER INFORMATION: Synthesized

<400> SEQUENCE: 144
ugguagggau gacaggauu                                            19

<210> SEQ ID NO 145
<211> LENGTH: 22
<212> TYPE: RNA
<213> ORGANISM: Artificial Sequence
<220> FEATURE:
<223> OTHER INFORMATION: Synthesized

<400> SEQUENCE: 145
uuuuauccau uaaacaauac cc                                        22

<210> SEQ ID NO 146
<211> LENGTH: 19
<212> TYPE: RNA
<213> ORGANISM: Artificial Sequence
<220> FEATURE:
<223> OTHER INFORMATION: Synthesized

<400> SEQUENCE: 146
uauccauuaa acaauaccc                                            19

<210> SEQ ID NO 147
<211> LENGTH: 22
<212> TYPE: RNA
<213> ORGANISM: Artificial Sequence
<220> FEATURE:
<223> OTHER INFORMATION: Synthesized

<400> SEQUENCE: 147
ugggcgggua gcgggaaucg aa                                        22

<210> SEQ ID NO 148
<211> LENGTH: 19
<212> TYPE: RNA
<213> ORGANISM: Artificial Sequence
<220> FEATURE:
<223> OTHER INFORMATION: Synthesized

<400> SEQUENCE: 148
ugggcgggua gcgggaauc                                            19

<210> SEQ ID NO 149
<211> LENGTH: 22
<212> TYPE: RNA
<213> ORGANISM: Artificial Sequence
<220> FEATURE:
<223> OTHER INFORMATION: Synthesized

<400> SEQUENCE: 149
uuagccacuc gggcaucgac cc                                        22

<210> SEQ ID NO 150
<211> LENGTH: 19
<212> TYPE: RNA
<213> ORGANISM: Artificial Sequence
<220> FEATURE:
<223> OTHER INFORMATION: Synthesized

<400> SEQUENCE: 150
gccacucggg caucgaccc                                            19
```

<210> SEQ ID NO 151
<211> LENGTH: 22
<212> TYPE: RNA
<213> ORGANISM: Artificial Sequence
<220> FEATURE:
<223> OTHER INFORMATION: Synthesized

<400> SEQUENCE: 151 ugguggggccg agcuggauuu ga                                            22

<210> SEQ ID NO 152
<211> LENGTH: 19
<212> TYPE: RNA
<213> ORGANISM: Artificial Sequence
<220> FEATURE:
<223> OTHER INFORMATION: Synthesized

<400> SEQUENCE: 152 ugguggggccg agcuggauu                                                19

<210> SEQ ID NO 153
<211> LENGTH: 22
<212> TYPE: RNA
<213> ORGANISM: Artificial Sequence
<220> FEATURE:
<223> OTHER INFORMATION: Synthesized

<400> SEQUENCE: 153
cuaccaauuc cgccauaucc cc                                             22

<210> SEQ ID NO 154
<211> LENGTH: 19
<212> TYPE: RNA
<213> ORGANISM: Artificial Sequence
<220> FEATURE:
<223> OTHER INFORMATION: Synthesized

<400> SEQUENCE: 154
ccaauuccgc cauaucccc                                                 19

<210> SEQ ID NO 155
<211> LENGTH: 22
<212> TYPE: RNA
<213> ORGANISM: Artificial Sequence
<220> FEATURE:
<223> OTHER INFORMATION: Synthesized

<400> SEQUENCE: 155 uggugggggau agagggacuu ga                                            22

<210> SEQ ID NO 156
<211> LENGTH: 19
<212> TYPE: RNA
<213> ORGANISM: Artificial Sequence
<220> FEATURE:
<223> OTHER INFORMATION: Synthesized

<400> SEQUENCE: 156 uggugggggau agagggacu                                                19

<210> SEQ ID NO 157
<211> LENGTH: 22
<212> TYPE: RNA
<213> ORGANISM: Artificial Sequence
<220> FEATURE:
<223> OTHER INFORMATION: Synthesized

```
<400> SEQUENCE: 157
ucaaccacuc ggccaucucu cc                                          22

<210> SEQ ID NO 158
<211> LENGTH: 19
<212> TYPE: RNA
<213> ORGANISM: Artificial Sequence
<220> FEATURE:
<223> OTHER INFORMATION: Synthesized

<400> SEQUENCE: 158
accacucggc caucucucc                                              19

<210> SEQ ID NO 159
<211> LENGTH: 22
<212> TYPE: RNA
<213> ORGANISM: Artificial Sequence
<220> FEATURE:
<223> OTHER INFORMATION: Synthesized

<400> SEQUENCE: 159
uggaggagag agagggauuc ga                                          22

<210> SEQ ID NO 160
<211> LENGTH: 19
<212> TYPE: RNA
<213> ORGANISM: Artificial Sequence
<220> FEATURE:
<223> OTHER INFORMATION: Synthesized

<400> SEQUENCE: 160
uggaggagag agagggauu                                              19

<210> SEQ ID NO 161
<211> LENGTH: 22
<212> TYPE: RNA
<213> ORGANISM: Artificial Sequence
<220> FEATURE:
<223> OTHER INFORMATION: Synthesized

<400> SEQUENCE: 161
ccuuaccgcu uggccacgcc cc                                          22

<210> SEQ ID NO 162
<211> LENGTH: 19
<212> TYPE: RNA
<213> ORGANISM: Artificial Sequence
<220> FEATURE:
<223> OTHER INFORMATION: Synthesized

<400> SEQUENCE: 162
uaccgcuugg ccacgcccc                                              19

<210> SEQ ID NO 163
<211> LENGTH: 22
<212> TYPE: RNA
<213> ORGANISM: Artificial Sequence
<220> FEATURE:
<223> OTHER INFORMATION: Synthesized

<400> SEQUENCE: 163
uggcugggac gaaaggauuc ga                                          22

<210> SEQ ID NO 164
```

```
<211> LENGTH: 19
<212> TYPE: RNA
<213> ORGANISM: Artificial Sequence
<220> FEATURE:
<223> OTHER INFORMATION: Synthesized

<400> SEQUENCE: 164
uggcugggac gaaaggauu                                                   19

<210> SEQ ID NO 165
<211> LENGTH: 22
<212> TYPE: RNA
<213> ORGANISM: Artificial Sequence
<220> FEATURE:
<223> OTHER INFORMATION: Synthesized

<400> SEQUENCE: 165
cuauccauua gacgauggac gc                                               22

<210> SEQ ID NO 166
<211> LENGTH: 19
<212> TYPE: RNA
<213> ORGANISM: Artificial Sequence
<220> FEATURE:
<223> OTHER INFORMATION: Synthesized

<400> SEQUENCE: 166
uccauuagac gauggacgc                                                   19

<210> SEQ ID NO 167
<211> LENGTH: 22
<212> TYPE: RNA
<213> ORGANISM: Artificial Sequence
<220> FEATURE:
<223> OTHER INFORMATION: Synthesized

<400> SEQUENCE: 167
ugguacgucc aauaggauuu ga                                               22

<210> SEQ ID NO 168
<211> LENGTH: 19
<212> TYPE: RNA
<213> ORGANISM: Artificial Sequence
<220> FEATURE:
<223> OTHER INFORMATION: Synthesized

<400> SEQUENCE: 168
ugguacgucc aauaggauu                                                   19

<210> SEQ ID NO 169
<211> LENGTH: 22
<212> TYPE: RNA
<213> ORGANISM: Artificial Sequence
<220> FEATURE:
<223> OTHER INFORMATION: Synthesized

<400> SEQUENCE: 169
uugaccauuc agccauggau gc                                               22

<210> SEQ ID NO 170
<211> LENGTH: 19
<212> TYPE: RNA
<213> ORGANISM: Artificial Sequence
<220> FEATURE:
<223> OTHER INFORMATION: Synthesized

<400> SEQUENCE: 170
```
accauucagc cauggaugc                                                    19

<210> SEQ ID NO 171
<211> LENGTH: 22
<212> TYPE: RNA
<213> ORGANISM: Artificial Sequence
<220> FEATURE:
<223> OTHER INFORMATION: Synthesized

<400> SEQUENCE: 171
uggugcaucc agcaggaauu ga                                                22

<210> SEQ ID NO 172
<211> LENGTH: 19
<212> TYPE: RNA
<213> ORGANISM: Artificial Sequence
<220> FEATURE:
<223> OTHER INFORMATION: Synthesized

<400> SEQUENCE: 172
uggugcaucc agcaggaau                                                    19

<210> SEQ ID NO 173
<211> LENGTH: 22
<212> TYPE: RNA
<213> ORGANISM: Artificial Sequence
<220> FEATURE:
<223> OTHER INFORMATION: Synthesized

<400> SEQUENCE: 173
cuaccaauuu caccauggcg gc                                                22

<210> SEQ ID NO 174
<211> LENGTH: 19
<212> TYPE: RNA
<213> ORGANISM: Artificial Sequence
<220> FEATURE:
<223> OTHER INFORMATION: Synthesized

<400> SEQUENCE: 174
ccaauuucac cauggcggc                                                    19

<210> SEQ ID NO 175
<211> LENGTH: 22
<212> TYPE: RNA
<213> ORGANISM: Artificial Sequence
<220> FEATURE:
<223> OTHER INFORMATION: Synthesized

<400> SEQUENCE: 175
uggugccacc acucggauuc ga                                                22

<210> SEQ ID NO 176
<211> LENGTH: 19
<212> TYPE: RNA
<213> ORGANISM: Artificial Sequence
<220> FEATURE:
<223> OTHER INFORMATION: Synthesized

<400> SEQUENCE: 176
uggugccacc acucggauu                                                    19

<210> SEQ ID NO 177
<211> LENGTH: 22
<212> TYPE: RNA

```
<213> ORGANISM: Artificial Sequence
<220> FEATURE:
<223> OTHER INFORMATION: Synthesized

<400> SEQUENCE: 177
ucuaccauug aguuaacaac cc                                              22

<210> SEQ ID NO 178
<211> LENGTH: 19
<212> TYPE: RNA
<213> ORGANISM: Artificial Sequence
<220> FEATURE:
<223> OTHER INFORMATION: Synthesized

<400> SEQUENCE: 178
accauugagu uaacaaccc                                                  19

<210> SEQ ID NO 179
<211> LENGTH: 22
<212> TYPE: RNA
<213> ORGANISM: Artificial Sequence
<220> FEATURE:
<223> OTHER INFORMATION: Synthesized

<400> SEQUENCE: 179
ugguggguug cccgggacuu ga                                              22

<210> SEQ ID NO 180
<211> LENGTH: 19
<212> TYPE: RNA
<213> ORGANISM: Artificial Sequence
<220> FEATURE:
<223> OTHER INFORMATION: Synthesized

<400> SEQUENCE: 180 uggugguug cccgggacu                                                   19

<210> SEQ ID NO 181
<211> LENGTH: 22
<212> TYPE: RNA
<213> ORGANISM: Artificial Sequence
<220> FEATURE:
<223> OTHER INFORMATION: Synthesized

<400> SEQUENCE: 181
cuaccaacug agcuaucccg ac                                              22

<210> SEQ ID NO 182
<211> LENGTH: 19
<212> TYPE: RNA
<213> ORGANISM: Artificial Sequence
<220> FEATURE:
<223> OTHER INFORMATION: Synthesized

<400> SEQUENCE: 182
ccaacugagc uaucccgac                                                  19

<210> SEQ ID NO 183
<211> LENGTH: 22
<212> TYPE: RNA
<213> ORGANISM: Artificial Sequence
<220> FEATURE:
<223> OTHER INFORMATION: Synthesized

<400> SEQUENCE: 183
uggugccagg aaccagauuu ga                                              22
```

<210> SEQ ID NO 184
<211> LENGTH: 19
<212> TYPE: RNA
<213> ORGANISM: Artificial Sequence
<220> FEATURE:
<223> OTHER INFORMATION: Synthesized

<400> SEQUENCE: 184
uggugccagg aaccagauu                                                19

<210> SEQ ID NO 185
<211> LENGTH: 22
<212> TYPE: RNA
<213> ORGANISM: Artificial Sequence
<220> FEATURE:
<223> OTHER INFORMATION: Synthesized

<400> SEQUENCE: 185
uaccaaacug cguuaugcuc cg                                            22

<210> SEQ ID NO 186
<211> LENGTH: 19
<212> TYPE: RNA
<213> ORGANISM: Artificial Sequence
<220> FEATURE:
<223> OTHER INFORMATION: Synthesized

<400> SEQUENCE: 186
caaacugcgu uaugcuccg                                                19

<210> SEQ ID NO 187
<211> LENGTH: 22
<212> TYPE: RNA
<213> ORGANISM: Artificial Sequence
<220> FEATURE:
<223> OTHER INFORMATION: Synthesized

<400> SEQUENCE: 187
uggucggagc aacaggauuu ga                                            22

<210> SEQ ID NO 188
<211> LENGTH: 19
<212> TYPE: RNA
<213> ORGANISM: Artificial Sequence
<220> FEATURE:
<223> OTHER INFORMATION: Synthesized

<400> SEQUENCE: 188
uggucggagc aacaggauu                                                19

<210> SEQ ID NO 189
<211> LENGTH: 22
<212> TYPE: RNA
<213> ORGANISM: Artificial Sequence
<220> FEATURE:
<223> OTHER INFORMATION: Synthesized

<400> SEQUENCE: 189
uaguccgcuc agccaucucu cc                                            22

<210> SEQ ID NO 190
<211> LENGTH: 19
<212> TYPE: RNA
<213> ORGANISM: Artificial Sequence
<220> FEATURE:

<223> OTHER INFORMATION: Synthesized

<400> SEQUENCE: 190
uccgcucagc caucucucc                                                19

<210> SEQ ID NO 191
<211> LENGTH: 22
<212> TYPE: RNA
<213> ORGANISM: Artificial Sequence
<220> FEATURE:
<223> OTHER INFORMATION: Synthesized

<400> SEQUENCE: 191
uggcggagaa agagggauuc ga                                            22

<210> SEQ ID NO 192
<211> LENGTH: 19
<212> TYPE: RNA
<213> ORGANISM: Artificial Sequence
<220> FEATURE:
<223> OTHER INFORMATION: Synthesized

<400> SEQUENCE: 192
uggcggagaa agagggauu                                                19

<210> SEQ ID NO 193
<211> LENGTH: 22
<212> TYPE: RNA
<213> ORGANISM: Artificial Sequence
<220> FEATURE:
<223> OTHER INFORMATION: Synthesized

<400> SEQUENCE: 193
ucuaccacug aguuaaaagu gc                                            22

<210> SEQ ID NO 194
<211> LENGTH: 19
<212> TYPE: RNA
<213> ORGANISM: Artificial Sequence
<220> FEATURE:
<223> OTHER INFORMATION: Synthesized

<400> SEQUENCE: 194
accacugagu uaaaagugc                                                19

<210> SEQ ID NO 195
<211> LENGTH: 22
<212> TYPE: RNA
<213> ORGANISM: Artificial Sequence
<220> FEATURE:
<223> OTHER INFORMATION: Synthesized

<400> SEQUENCE: 195
uggagcccuu uaucgggcuu ga                                            22

<210> SEQ ID NO 196
<211> LENGTH: 19
<212> TYPE: RNA
<213> ORGANISM: Artificial Sequence
<220> FEATURE:
<223> OTHER INFORMATION: Synthesized

<400> SEQUENCE: 196
uggagcccuu uaucgggcu                                                19

```
<210> SEQ ID NO 197
<211> LENGTH: 22
<212> TYPE: RNA
<213> ORGANISM: Artificial Sequence
<220> FEATURE:
<223> OTHER INFORMATION: Synthesized

<400> SEQUENCE: 197
ucuacuacug aguuauaucc cu                                                    22

<210> SEQ ID NO 198
<211> LENGTH: 19
<212> TYPE: RNA
<213> ORGANISM: Artificial Sequence
<220> FEATURE:
<223> OTHER INFORMATION: Synthesized

<400> SEQUENCE: 198
acuacugagu uauaucccu                                                        19

<210> SEQ ID NO 199
<211> LENGTH: 22
<212> TYPE: RNA
<213> ORGANISM: Artificial Sequence
<220> FEATURE:
<223> OTHER INFORMATION: Synthesized

<400> SEQUENCE: 199
ugguagggau aaucagguuu ga                                                    22

<210> SEQ ID NO 200
<211> LENGTH: 19
<212> TYPE: RNA
<213> ORGANISM: Artificial Sequence
<220> FEATURE:
<223> OTHER INFORMATION: Synthesized

<400> SEQUENCE: 200
ugguagggau aaucagguu                                                        19

<210> SEQ ID NO 201
<211> LENGTH: 78
<212> TYPE: RNA
<213> ORGANISM: Taxus chinensis (Pilger) Rehd. var. mairei.

<400> SEQUENCE: 201
gcggacguag ccaagugguc caaaggcagu ggauugugaa uccaccacgc gcgguucaa            60 uccccgucgu ucgcccca                                                         78

<210> SEQ ID NO 202
<211> LENGTH: 76
<212> TYPE: RNA
<213> ORGANISM: Taxus chinensis (Pilger) Rehd. var. mairei.

<400> SEQUENCE: 202
gccccuaucg ucuaguggcc caggacaucu cucuuucaag gaggcaacgg ggauucgauu           60
uccccuaggg guacca                                                           76

<210> SEQ ID NO 203
<211> LENGTH: 75
<212> TYPE: RNA
<213> ORGANISM: Taxus chinensis (Pilger) Rehd. var. mairei.

<400> SEQUENCE: 203
```

-continued

```
gcgcucuuag uucagugcgg uagaacgcag gucuccaaaa ccugaugccg uagguucaaa    60
uccuacagag cgcca                                                     75

<210> SEQ ID NO 204
<211> LENGTH: 84
<212> TYPE: RNA
<213> ORGANISM: Taxus chinensis (Pilger) Rehd. var. mairei.

<400> SEQUENCE: 204
gccuugaugg ugaaauggua gacacgcgag acucaaaauc ucgugcuaaa cagcguggag    60
guucgaaucc ucuucaaggc acca                                           84

<210> SEQ ID NO 205
<211> LENGTH: 77
<212> TYPE: RNA
<213> ORGANISM: Taxus chinensis (Pilger) Rehd. var. mairei.

<400> SEQUENCE: 205
gggccuguag cucagaggau uagagcacgu gguugcgaac cacgugucg ggguucgaa     60 ucccuccucg cccacca                                                   77

<210> SEQ ID NO 206
<211> LENGTH: 77
<212> TYPE: RNA
<213> ORGANISM: Taxus chinensis (Pilger) Rehd. var. mairei.

<400> SEQUENCE: 206
gggauuguag uucaauuggu uagaguaccg cccugucaag acggaaguug cggguucgag    60
ccccgucagu cccgcca                                                   77

<210> SEQ ID NO 207
<211> LENGTH: 75
<212> TYPE: RNA
<213> ORGANISM: Taxus chinensis (Pilger) Rehd. var. mairei.

<400> SEQUENCE: 207
uccucaguag cucaguggua gagcggucgg cuguuaaccg auuggucgua gguucaaauc    60
cuauuugagg agcca                                                     75

<210> SEQ ID NO 208
<211> LENGTH: 74
<212> TYPE: RNA
<213> ORGANISM: Taxus chinensis (Pilger) Rehd. var. mairei.

<400> SEQUENCE: 208
ggcgacauag ccaaguggua aggcagggga cugcaaaucc cccaucccca guucaaaucc    60
gggugucgcc ucca                                                      74

<210> SEQ ID NO 209
<211> LENGTH: 75
<212> TYPE: RNA
<213> ORGANISM: Taxus chinensis (Pilger) Rehd. var. mairei.

<400> SEQUENCE: 209
ggggcguggc caagcgguaa ggcaacaggu uuggguccug uuauugcgaa gguucgaauc    60
cuuucguccc agcca                                                     75

<210> SEQ ID NO 210
<211> LENGTH: 72
```

```
<212> TYPE: RNA
<213> ORGANISM: Taxus chinensis (Pilger) Rehd. var. mairei.

<400> SEQUENCE: 210
ggguauuguu uaauggauaa aauuuauucu ugccaaggau aagaugcggg uucgauuccc    60
gcuacccgcc ca                                                       72

<210> SEQ ID NO 211
<211> LENGTH: 75
<212> TYPE: RNA
<213> ORGANISM: Taxus chinensis (Pilger) Rehd. var. mairei.

<400> SEQUENCE: 211
agggauauaa cucaguagua gagugucacc uuuauguggu gaaagucauc aguucaaacc    60
ugauuauccc uacca                                                    75

<210> SEQ ID NO 212
<211> LENGTH: 83
<212> TYPE: RNA
<213> ORGANISM: Taxus chinensis (Pilger) Rehd. var. mairei.

<400> SEQUENCE: 212
gccgccaugg ugaaauuggu agacacgcug cucuuaggaa gcagugcuag agcaucucgg    60
uucgaauccg aguggguggca cca                                          83

<210> SEQ ID NO 213
<211> LENGTH: 90
<212> TYPE: RNA
<213> ORGANISM: Taxus chinensis (Pilger) Rehd. var. mairei.

<400> SEQUENCE: 213
ggggauaugg cggaauuggu agacgcuacg gacuuaaaaa auccguuggu uuuauaaacc    60 gugagggguuc aagucccucu auccccacca                                   90

<210> SEQ ID NO 214
<211> LENGTH: 75
<212> TYPE: RNA
<213> ORGANISM: Taxus chinensis (Pilger) Rehd. var. mairei.

<400> SEQUENCE: 214
ggguuguuaa cucaauggua gaguacucgg cuuuuaaccg acgaguuccg ggucaaguc    60 ccgggcaacc cacca                                                    75

<210> SEQ ID NO 215
<211> LENGTH: 76
<212> TYPE: RNA
<213> ORGANISM: Taxus chinensis (Pilger) Rehd. var. mairei.

<400> SEQUENCE: 215
gcauccaugg cugaauggu aaagcaccca acucauaauu gggaagucgc ggguucaauu    60
ccugcuggau gcacca                                                   76

<210> SEQ ID NO 216
<211> LENGTH: 77
<212> TYPE: RNA
<213> ORGANISM: Taxus chinensis (Pilger) Rehd. var. mairei.

<400> SEQUENCE: 216
cgcggaguag agcaguuugg uagcucgcaa ggcucauaac cuugaaguca cgggguucaaa   60
```

```
ucccgucucc gcaacca                                                  77

<210> SEQ ID NO 217
<211> LENGTH: 76
<212> TYPE: RNA
<213> ORGANISM: Taxus chinensis (Pilger) Rehd. var. mairei.

<400> SEQUENCE: 217
gucgggauag cucaguuggu agagcagagg acugaaaauc cucgugucac caguucaaau   60
cugguuccug gcacca                                                   76

<210> SEQ ID NO 218
<211> LENGTH: 77
<212> TYPE: RNA
<213> ORGANISM: Taxus chinensis (Pilger) Rehd. var. mairei.

<400> SEQUENCE: 218
agggauguag cgcagcuugg uagcgcguuu guuugggua caaaaugucg cagguucaaa    60
uccugucauc ccuacca                                                  77

<210> SEQ ID NO 219
<211> LENGTH: 77
<212> TYPE: RNA
<213> ORGANISM: Taxus chinensis (Pilger) Rehd. var. mairei.

<400> SEQUENCE: 219
cggagcauaa cgcaguuugg uagcgugcca ucuuggggug auggaggucg cgguucaaa    60 uccuguugcu ccgacca                                                  77

<210> SEQ ID NO 220
<211> LENGTH: 91
<212> TYPE: RNA
<213> ORGANISM: Taxus chinensis (Pilger) Rehd. var. mairei.

<400> SEQUENCE: 220
ggagagaugg ccgagugguu gauggcuccg gucuugaaaa ccgguauagu uuuaaaaacu   60
aucgaggguu cgaaucccuc ucucuccucc a                                  91

<210> SEQ ID NO 221
<211> LENGTH: 91
<212> TYPE: RNA
<213> ORGANISM: Taxus chinensis (Pilger) Rehd. var. mairei.

<400> SEQUENCE: 221
ggagagaugg cugagcggac uaaagcggug gauugcuaau ccguuguaca gacuaucugu   60
accgagdguu cgaaucccuc uuucuccgcc a                                  91

<210> SEQ ID NO 222
<211> LENGTH: 76
<212> TYPE: RNA
<213> ORGANISM: Taxus chinensis (Pilger) Rehd. var. mairei.

<400> SEQUENCE: 222
gccugcuuag cucagagguu agagcaucgc acuuguaaug cgacggucau cgguucgauc   60
ccgauagaag gcucca                                                   76

<210> SEQ ID NO 223
<211> LENGTH: 75
<212> TYPE: RNA
<213> ORGANISM: Taxus chinensis (Pilger) Rehd. var. mairei.
```

```
<400> SEQUENCE: 223
gcacuuuuaa cucaguggua gaguaacgcc augguaaggc guaagucauc gguucaagcc        60
cgauaaaggg cucca                                                        75

<210> SEQ ID NO 224
<211> LENGTH: 87
<212> TYPE: RNA
<213> ORGANISM: Taxus chinensis (Pilger) Rehd. var. mairei.

<400> SEQUENCE: 224
gggucgaugc ccgaguggcu aauggggacg gacuguaaau ccguuggcaa uaugcuuacg        60
cugguucaaa uccagcucgg cccacca                                           87

<210> SEQ ID NO 225
<211> LENGTH: 75
<212> TYPE: RNA
<213> ORGANISM: Taxus chinensis (Pilger) Rehd. var. mairei.

<400> SEQUENCE: 225
gcguccaucg ucuaauggau aggacagagg ucuucuaaac cuuagguaua gguucaaauc        60
cuauuggacg uacca                                                        75
```